US012807656B2

(12) United States Patent
Park et al.

(10) Patent No.: US 12,807,656 B2
(45) Date of Patent: Nov. 24, 2026

(54) YhhS VARIANT AND METHOD FOR PRODUCING O-PHOSPHOSERINE, CYSTEINE, AND DERIVATE OF CYSTEINE USING SAME

(71) Applicant: CJ CHEILJEDANG CORPORATION, Seoul (KR)

(72) Inventors: Hye Min Park, Seoul (KR); Hee-jin Sim, Seoul (KR); Hwi-Min Jung, Seoul (KR); Jin Nam Lee, Seoul (KR); Jin-Geun Choi, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 354 days.

(21) Appl. No.: 18/691,839

(22) PCT Filed: Jun. 3, 2022

(86) PCT No.: PCT/KR2022/007930
§ 371 (c)(1),
(2) Date: Mar. 13, 2024

(87) PCT Pub. No.: WO2022/255839
PCT Pub. Date: Dec. 8, 2022

(65) Prior Publication Data

US 2025/0376493 A1 Dec. 11, 2025

(30) Foreign Application Priority Data

Jun. 3, 2021 (KR) ........................ 10-2021-0072313

(51) Int. Cl.

| | |
|---|---|
| ***C07K 14/245*** | (2006.01) |
| ***C12N 1/20*** | (2026.01) |
| ***C12N 9/16*** | (2006.01) |
| *C12R 1/19* | (2006.01) |

(52) U.S. Cl.
CPC .............. *C07K 14/245* (2013.01); *C12N 1/20* (2013.01); *C12N 9/16* (2013.01); *C12R 2001/19* (2021.05); *C12Y 301/03003* (2013.01)

(58) Field of Classification Search
CPC ........... C07K 14/245; C12N 1/20; C12N 9/16
See application file for complete search history.

(56) References Cited

U.S. PATENT DOCUMENTS

| | | | |
|---|---|---|---|
| 2003/0008358 | A1 | 1/2003 | Suga et al. |
| 2016/0370381 | A1 | 12/2016 | Li et al. |
| 2020/0318163 | A1 | 10/2020 | Chegounian et al. |

FOREIGN PATENT DOCUMENTS

| | | | |
|---|---|---|---|
| EP | 3181685 | A1 | 6/2017 |
| JP | 2017-528126 | A | 9/2017 |
| JP | 2018-526017 | A | 9/2018 |
| KR | 10-2014-0133754 | A | 11/2014 |
| KR | 10-1677328 | B1 | 11/2016 |
| KR | 10-1694632 | B1 | 1/2017 |
| WO | 2021/013708 | A1 | 1/2021 |

OTHER PUBLICATIONS

NCBI GenBank, "UPF0226 protein yhhS [*Escherichia coli* M919]", Accession No. EIF84903.1, Apr. 27, 2012 , 1 page.
NCBI GenBank, "MFS transporter [*Escherichia coli*]", GenPept, Accession No. QHF76583. 1, May 26, 2020, 2 pages.
Office Action issued in corresponding Canadian Patent Application No. 3,231,648, dated Aug. 1, 2025.
Lewis et al., "Association of ISVsa3 with Multidrug Resistance in *Salmonella enterica* Isolates from Cattle (*Bos taurus*)", Microorganisms, vol. 11, No. 631, 2023, pp. 1-15.
Yan, "Structural Biology of the Major Facilitator Superfamily Transporters", Annu Rev Biophys, vol. 44, 2015, 1 page.
Office Action issued in corresponding Australian Patent Application No. 2022286220, dated Jun. 2, 2025.
NCBI GenBank Database, "Uncharacterized MFS-type transporter YhhS", Uniprot, Accession No. A0A630S302, Apr. 22, 2020, pp. 1-2.
NCBI GenBank Database, "Uncharacterized MFS-type transporter YhhS", Uniprot, Accession No. A0A3U8MKX4, Jul. 31, 2019, pp. 1-3.
Prasad et al., "Functionally Relevant Residues of Cdrlp: A Multidrug ABC Transporter of Human Pathogenic Candida albicans", Journal of Amino Acids, vol. 2011, Article ID 531412, pp. 1-12.
Zhang et al., "Energy coupling mechanisms of MFS transporters", Protein Science, vol. 24, 2015 pp. 1560-1579.
Office Action issued in corresponding Japanese Patent Application No. 2024-526583, dated May 7, 2025.
NCBI GenBank, "Major facilitator superfamily [*Pseudomonas syringae* pv. syringae B728a]", GenPept, Accession No. AAY37532.1, Jan. 31, 2014, pp. 1-2.
UniProtKB/TrEMBL, "Uncharacterized MFS-type transporter PS862_04695", Gene, A0A5E7NM34, yhhS, Sep. 2019, https://www.uniprot.org/uniprotkb/AOA5E7NM34/entry, pp. 1-6.
Extended European Search Report issued in corresponding European Patent Application No. 22816498.4, dated Oct. 27, 2025.

*Primary Examiner* — Prema M Mertz
(74) *Attorney, Agent, or Firm* — Morgan, Lewis & Bockius LLP

(57) ABSTRACT

The present disclosure relates to a novel YhhS variant and a method for producing O-phosphoserine, cysteine and a derivative of cysteine using the same.

19 Claims, No Drawings

Specification includes a Sequence Listing.

YhhS VARIANT AND METHOD FOR PRODUCING O-PHOSPHOSERINE, CYSTEINE, AND DERIVATE OF CYSTEINE USING SAME

A computer readable text file, entitled "133660-04-9036-US_Sequence_Listing_ST25.txt," created on or about Jul. 6, 2026, with a file size of 5,8000 bytes contains the sequence listing for this application and is hereby incorporated by reference in its entirety.

TECHNICAL FIELD

The present disclosure relates to a YhhS variant and a method for producing O-phosphoserine, cysteine and a derivative of cysteine using the same.

BACKGROUND ART

L-cysteine is an important amino acid for sulfur metabolism in all living things, and is used not only in the synthesis of in vivo proteins such as hair keratin, glutathione, biotin, methionine and other sulfur-containing metabolites but also as a precursor in coenzyme A biosynthesis.

As a method for producing L-cysteine using a microorganism, 1) a method in which D,L-ATC (D,L-2-aminothiazoline-4-carboxylic acid) is biologically converted using a microorganism, 2) a direct fermentation method in which L-cysteine is produced using *E. coli* (EP 0885962 B; Wada M and Takagi H, *Appl. Microbiol. Biochem.,* 73:48-54, 2006), and 3) a method in which O-phosphoserine (OPS) is produced by fermentation using a microorganism and then reacted with a sulfide by the catalysis of O-phosphoserine sulfhydrylase (OPSS) to be converted into L-cysteine (U.S. Pat. No. 8,557,549 B2) are known.

At this time, in order to produce cysteine at a high yield by the method 3), it is required to produce an excessive amount of OPS, a precursor.

DISCLOSURE

Technical Problem

The present inventors completed the present disclosure by identifying a variant of a membrane protein exhibiting activity capable of exporting OPS out of a cell, and confirming that exporting OPS is improved due to the variant.

Technical Solution

An object of the present disclosure is to provide a YhhS variant in which an amino acid corresponding to the 129th position in the amino acid sequence of SEQ ID NO: 1 is substituted with another amino acid.

Another object of the present disclosure is to provide a YhhS variant in which isoleucine, an amino acid corresponding to the 241st position in the amino acid sequence of SEQ ID NO: 1, is substituted with glutamine.

Still another object of the present disclosure is to provide a polynucleotide encoding the variant of the present disclosure.

Still another object of the present disclosure is to provide a microorganism of the genus *Escherichia*, comprising the variant of the present disclosure or a polynucleotide encoding the variant.

Still another object of the present disclosure is to provide a method for producing O-phosphoserine, which comprises culturing a microorganism containing the variant of the present disclosure or a polynucleotide encoding the variant in a medium.

Still another object of the present disclosure is to provide a method for producing cysteine or a derivative cysteine, which comprises a) culturing an O-phosphoserine-producing microorganism containing the variant of the present disclosure or a polynucleotide encoding the variant in a medium to produce O-phosphoserine or a O-phosphoserine-containing medium; and b) bringing O-phosphoserine sulfhydrylase (OPSS) or a microorganism expressing O-phosphoserine sulfhydrylase, the O-phosphoserine or O-phosphoserine-containing medium produced in the step a), and a sulfide into contact with one another.

Advantageous Effects

When a microorganism having the OPS producing ability is cultured using the novel mutant polypeptide exhibiting O-phosphoserine (OPS) exporting activity of the present disclosure, it is possible to produce OPS at a higher yield compared to the case of using the existing unmodified or mutant protein.

BEST MODE

This will be described in detail as follows. Meanwhile, each description and embodiment disclosed in the present disclosure may be applied to other descriptions and embodiments. That is, all combinations of the various elements disclosed in the present disclosure fall within the scope of the present disclosure. In addition, the scope of the present disclosure is not limited by the detailed description below.

In addition, a number of papers and patent documents are referenced throughout the present specification and their citations are indicated. The disclosure contents of the cited papers and patent documents are incorporated herein by reference in their entirety to more clearly describe the level of the technical field to which the present invention pertains and the contents of the present invention.

An aspect of the present disclosure provides a YhhS variant in which an amino acid corresponding to a 129th position of an amino acid sequence of SEQ ID NO: 1 is substituted with another amino acid.

As used herein, the term "YhhS" refers to a polypeptide exhibiting O-phosphoserine (OPS) exporting activity, specifically, a membrane protein exhibiting activity capable of exporting OPS out of a cell. In the present disclosure, YhhS may be a YhhS MFS (major facilitator superfamily) transporter, a membrane protein exhibiting activity capable of exporting OPS out of a cell. The YhhS has been identified as a protein exhibiting OPS exporting activity from *E. coli* in which the growth inhibition is released under conditions in which an excessive amount of OPS is present.

As used herein, the term "O-phosphoserine (OPS)" is a phosphoric acid ester of serine, and is a component of several proteins. OPS is a precursor of L-cysteine, and may be converted into cysteine by reacting with a sulfide by the catalysis of OPS sulfhydrylase (OPSS), but is not limited thereto (U.S. Pat. No. 8,557,549 B2).

Specifically, YhhS of the present disclosure may be used interchangeably with the YhhS MFS transporter. In the present disclosure, the amino acid sequence of YhhS may be obtained from GenBank of NCBI, a known database. The amino acid sequence may be specifically a polypeptide exhibiting YhhS activity encoded by the yhhS gene, more specifically SEQ ID NO: 1, but is not limited thereto.

The amino acid corresponding to the 129th position in the amino acid sequence of SEQ ID NO: 1 may be a polar amino acid. The polar amino acid may be, for example, serine, threonine, cysteine, tyrosine, asparagine, or glutamine, and specifically serine.

In the variant of the present disclosure, the polar amino acid corresponding to the 129th position based on the amino acid sequence of SEQ ID NO: 1 may be substituted with a non-polar amino acid. The non-polar amino acid may be, for example, glycine, alanine, valine, leucine, isoleucine, methionine, phenylalanine, tryptophan or proline, and specifically glycine or alanine. The variant may include an amino acid sequence having at least 70%, 75%, 80%, 85%, 90%, 95%, 96%, 97%, 98%, 99%, 99.5%, 99.7%, or 99.9% or more homology or identity to an amino acid sequence in which the amino acid corresponding to the 129th position based on the amino acid sequence of SEQ ID NO: 1 is glycine or alanine. It is apparent that variants having an amino acid sequence in which part of the sequence is deleted, modified, substituted, conservatively substituted, or added are also included within the scope of the present disclosure as long as the amino acid sequence has such homology or identity and exhibits efficacy corresponding to that of the variant of the present disclosure.

For example, addition or deletion of sequences, naturally occurring mutations, silent mutations or conservative substitutions, which do not alter the function of the variant of the present disclosure in the N-terminus, C-terminus and/or inside of the amino acid sequence, may be included.

As used herein, the term "conservative substitution" means substituting an amino acid with another amino acid exhibiting similar structural and/or chemical properties. The variant may have, for example, one or more conservative substitutions while still retaining one or more biological activities. Such amino acid substitutions may generally occur based on similarity in polarity, charge, solubility, hydrophobicity, hydrophilicity and/or amphipathic nature of the residues. For example, among electrically charged amino acids, positively charged (basic) amino acids include arginine, lysine, and histidine and negatively charged (acidic) amino acids include glutamic acid and aspartic acid; among uncharged amino acids, nonpolar amino acids include glycine, alanine, valine, leucine, isoleucine, methionine, phenylalanine, tryptophan, and proline and polar or hydrophilic amino acids include serine, threonine, cysteine, tyrosine, asparagine, and glutamine; and among the amino acids, aromatic amino acids include phenylalanine, tryptophan, and tyrosine.

As used herein, the term "variant" refers to a polypeptide in which one or more amino acids are conservatively substituted and/or modified so that the amino acid sequence differs from that before the mutation of the variant but the functions or properties are maintained. Such a variant may generally be identified by modifying one or more amino acids in the amino acid sequence of the polypeptide and evaluating the properties of the modified polypeptide. In other words, the ability of the variant may be enhanced, unchanged, or decreased compared to that of the polypeptide before the mutation. Some variants may include variants from which one or more portions, such as an N-terminal leader sequence or a transmembrane domain, have been removed. Other variants may include variants in which a portion has been removed from the N- and/or C-terminus of the mature protein. The term "variant" may be used interchangeably with terms such as modification, modified polypeptide, modified protein, mutant, mutein, and divergent, and is not limited thereto as long as it is a term used in a mutated sense. For the purposes of the present disclosure, the variant may be a polypeptide including the amino acid sequence set forth in SEQ ID NO: 1 in which serine, an amino acid corresponding to the 129th position in the amino acid sequence of SEQ ID NO: 1, is substituted with glycine or alanine.

Additionally, the variant may contain deletions or additions of amino acids that have a minimal effect on the secondary structure and properties of the polypeptide. For example, a signal (or leader) sequence involved in protein translocation may be conjugated to the N-terminus of the variant either co-translationally or post-translationally. The variant may be conjugated to other sequences or linkers for identification, purification, or synthesis.

As used herein, the term "homology" or "identity" refers to the degree of similarity between two given amino acid sequences or nucleotide sequences, and may be expressed as a percentage. The terms homology and identity may often be used interchangeably.

The sequence homology or identity of a conserved polynucleotide or polypeptide is determined by standard alignment algorithms, and default gap penalties established by the program being used may be used together. Substantially homologous or identical sequences are generally capable of hybridizing with all or part of the sequences under moderate or high stringent conditions. It is obvious that hybridization also includes hybridization with a polynucleotide containing a common codon in a polynucleotide or a codon in consideration of codon degeneracy.

Whether arbitrary two polynucleotide or polypeptide sequences have homology, similarity or identity may be determined, for example, using known computer algorithms such as the "FASTA" program using default parameters as in Pearson et al. (1988) [*Proc. Natl. Acad. Sci. USA* 85]: 2444. Alternatively, whether arbitrary two polynucleotide or polypeptide sequences have homology, similarity or identity may be determined using the Needleman-Wunsch algorithm (Needleman and Wunsch, 1970, *J. Mol. Biol.* 48:443-453) as performed in the Needleman program of the EMBOSS package (EMBOSS: The European Molecular Biology Open Software Suite, Rice et al., 2000, *Trends Genet.* 16:276-277) (version 5.0.0 or later) (including GCG program package (Devereux, J., et al.,*Nucleic Acids Research* 12:387 (1984)), BLASTP, BLASTN, FASTA (Atschul, [S.][F.,][et al., *J Molec Biol* 215]: 403 (1990); Guide to Huge Computers, Martin J. Bishop, [ED.,] Academic Press, San Diego, 1994, and [CARILLO et al.] (1988) SIAM *J Applied Math* 48:1073). For example, BLAST of the National Center for Biotechnology Information Database, or ClustalW may be used to determine homology, similarity or identity.

The homology, similarity, or identity of polynucleotides or polypeptides may be determined by comparing sequence information using, for example, a GAP computer program such as Needleman et al. (1970), *J Mol Biol.* 48:443 as known in, for example, Smith and Waterman, *Adv. Appl. Math* (1981) 2:482. In summary, a GAP program may be defined as the value acquired by dividing the total number of symbols in the shorter of two sequences by the number of similarly aligned symbols (namely, nucleotides or amino acids). The default parameters for the GAP program may include (1) a binary comparison matrix (containing values of 1 for identity and 0 for non-identity) and a weighted comparison matrix of Gribskov et al. (1986) *Nucl. Acids Res.* 14:6745 (or EDNAFULL (EMBOSS version of NCBI NUC4.4) substitution matrix) as disclosed by Schwartz and Dayhoff, eds., Atlas Of Protein Sequence And Structure, National Biomedical Research Foundation, pp. 353-358

(1979); (2) a penalty of 3.0 for each gap and an additional penalty of 0.10 for each symbol in each gap (or a gap opening penalty of 10, a gap extension penalty of 0.5); and (3) no penalty for an end gap.

As used herein, the term "corresponding to" refers to an amino acid residue at a listed position in a polypeptide, or an amino acid residue that is similar, identical, or homologous to a residue listed in a polypeptide. Identifying the amino acid at the corresponding position may be determining a specific amino acid of a sequence that refers to a specific sequence. As used herein, the term "corresponding region" generally refers to a similar or corresponding position in a related or reference protein.

For example, an arbitrary amino acid sequence is aligned with SEQ ID NO: 1, and based on this, each amino acid residue of the amino acid sequence may be numbered with reference to the numerical position of the amino acid residue corresponding to the amino acid residue in SEQ ID NO: 1. For example, a sequence alignment algorithm as described in the present disclosure may be compared to a query sequence (also referred to as a "reference sequence") to determine the position of an amino acid, or a position where modifications, such as substitutions, insertions, or deletions, occur.

For such alignment, for example, the Needleman-Wunsch algorithm (Needleman and Wunsch, 1970, *J. Mol. Biol.* 48:443-453), the Needleman program of the EMBOSS package (EMBOSS: The European Molecular Biology Open Software Suite, Rice et al., 2000), and *Trends Genet.* 16:276-277) may be used, but the program is not limited thereto, and a sequence alignment program, a pairwise sequence comparison algorithm, and the like known in the art may be appropriately used.

Another aspect of the present disclosure is to provide a YhhS variant in which isoleucine, an amino acid corresponding to a 241st position in an amino acid sequence of SEQ ID NO: 1, is substituted with glutamine or threonine.

The "amino acid sequence of SEQ ID NO: 1", "YhhS" and "variant" are as described in the other aspect above.

Specifically, in the variant of the present disclosure, isoleucine, an amino acid corresponding to the 241st position based on the amino acid sequence of SEQ ID NO: 1, is substituted with glutamine or threonine. The variant may include an amino acid sequence having at least 70%, 75%, 80%, 85%, 90%, 95%, 96%, 97%, 98%, 99%, 99.5%, 99.7%, or 99.9% or more homology or identity to an amino acid sequence in which the amino acid corresponding to the 241st position based on the amino acid sequence of SEQ ID NO: 1 is glutamine or threonine, and this is as described in the other aspect above.

In the variant of the present disclosure, the amino acid corresponding to the 129th position in the amino acid sequence of SEQ ID NO: 1 may be substituted with another amino acid, and further isoleucine, an amino acid corresponding to the 241st position, may be substituted with glutamine or threonine.

In addition to the substitution of the amino acid corresponding to the 129th position or 241st position in the amino acid sequence of SEQ ID NO: 1, the variant of the present disclosure may contain further substitution of aspartic acid, an amino acid corresponding to the 246th position in the amino acid sequence of SEQ ID NO: 1, with valine and/or further substitution of valine, an amino acid corresponding to the 330th position in the amino acid sequence of SEQ ID NO: 1, with isoleucine.

In addition, in the variant of the present disclosure, the amino acid corresponding to the 88th position in the amino acid sequence of SEQ ID NO: 1 may be phenylalanine and the amino acid corresponding to the 207th position in the amino acid sequence of SEQ ID NO: 1 may be lysine.

Specifically, the variant of the present disclosure may include an amino acid sequence of SEQ ID NO: 2 in which serine, an amino acid corresponding to the 129th position in the amino acid sequence of SEQ ID NO: 1, is substituted with glycine; SEQ ID NO: 3 in which serine, an amino acid corresponding to the 129th position in the amino acid sequence of SEQ ID NO: 1, is substituted with alanine; SEQ ID NO: 4 in which isoleucine, an amino acid corresponding to the 241st position in the amino acid sequence of SEQ ID NO: 1, is substituted with glutamine; SEQ ID NO: 5 in which isoleucine, an amino acid corresponding to the 241st position in the amino acid sequence of SEQ ID NO: 1, is substituted with threonine; SEQ ID NO: 12 in which isoleucine, an amino acid corresponding to the 241st position in the amino acid sequence of SEQ ID NO: 1, is substituted with threonine, aspartic acid, an amino acid corresponding to the 246th position, is substituted with valine, and valine, an amino acid corresponding to the 330th position, is substituted with isoleucine; SEQ ID NO: 34 in which serine, an amino acid corresponding to the 129th position in the amino acid sequence of SEQ ID NO: 1, is substituted with glycine; isoleucine, an amino acid corresponding to the 241st position, is substituted with threonine, aspartic acid, an amino acid, corresponding to the 246th position, is substituted with valine, and valine, an amino acid corresponding to the 330th position, is substituted with isoleucine; or SEQ ID NO: 36 in which serine, an amino acid corresponding to the 129th position in the amino acid sequence of SEQ ID NO: 1, is substituted with glycine and isoleucine, an amino acid corresponding to the 241st position, is substituted with glutamine.

The variant of the present disclosure may consist of the amino acid sequence of SEQ ID NO: 2 or SEQ ID NO: 3 or SEQ ID NO: 4 or SEQ ID NO: 5 or SEQ ID NO: 12 or SEQ ID NO: 34 or SEQ ID NO: 36, or may be a polypeptide including the amino acid sequence.

Additionally, the variant of the present disclosure may have 99% or more sequence identity (homology or identity) to the amino acid sequence of SEQ ID NO: 2 or SEQ ID NO: 3 or SEQ ID NO: 4 or SEQ ID NO: 5 or SEQ ID NO: 12 or SEQ ID NO: 34 or SEQ ID NO: 36, but may have at least 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more or less than 100% sequence identity to the amino acid sequence of SEQ ID NO: 2 or SEQ ID NO: 3 or SEQ ID NO: 4 or SEQ ID NO: 5 or SEQ ID NO: 12 or SEQ ID NO: 34 or SEQ ID NO: 36. It is apparent that variants having an amino acid sequence in which some sequences are deleted, modified, substituted, conservatively substituted, or added are also included within the scope of the present disclosure as long as the amino acid sequence has such homology or identity and exhibits efficacy corresponding to that of the variant of the present disclosure.

As an example of the present disclosure, the variant of the present disclosure may exhibit YhhS activity. The variant of the present disclosure may exhibit activity to increase OPS export compared to the wild-type polypeptide.

YhhS is as described in the other aspects above.

Still another aspect of the present disclosure is to provide a polynucleotide encoding the variant of the present disclosure.

The "variant" is as described above.

As used herein, the term "polynucleotide" refers to a DNA or RNA strand of a certain length or longer as a polymer of nucleotides in which nucleotide monomers are linked in a long chain by covalent bonds, and more specifically refers to a polynucleotide fragment encoding the variant.

The polynucleotide encoding the variant of the present disclosure may include a nucleotide sequence encoding the amino acid sequence set forth in SEQ ID NO: 2 or SEQ ID NO: 3 or SEQ ID NO: 4 or SEQ ID NO: 5 or SEQ ID NO: 12 or SEQ ID NO: 34 or SEQ ID NO: 36. As an example of the present disclosure, the polynucleotide of the present disclosure may have or include the sequence of SEQ ID NO: 6 or SEQ ID NO: 7 or SEQ ID NO: 8 or SEQ ID NO: 9 or SEQ ID NO: 17 or SEQ ID NO: 35 or SEQ ID NO: 37. The polynucleotide of the present disclosure may consist of or consist essentially of the sequence of SEQ ID NO: 6 or SEQ ID NO: 7 or SEQ ID NO: 8 or SEQ ID NO: 9 or SEQ ID NO: 17 or SEQ ID NO: 35 or SEQ ID NO: 37.

In the polynucleotide of the present disclosure, various modifications may be made in the coding region within a range in which the amino acid sequence of the variant of the present disclosure is not changed in consideration of codon degeneracy or preferred codons in the organism to express the variant of the present disclosure. Specifically, the polynucleotide of the present disclosure may have or include a nucleotide sequence having 70% or more, 75% or more, 80% or more, 85% or more, 90% or more, 95% or more, 96% or more, 97% or more, or 98% or more and less than 100% homology or identity to the sequence of SEQ ID NO: 6 or SEQ ID NO: 7 or SEQ ID NO: 8 or SEQ ID NO: 9 or SEQ ID NO: 17 or SEQ ID NO: 35 or SEQ ID NO: 37, or may consist of or consist essentially of a nucleotide sequence having 70% or more, 75% or more, 80% or more, 85% or more, 90% or more, 95% or more, 96% or more, 97% or more, or 98% or more and less than 100% homology or identity to the sequence of SEQ ID NO: 6 or SEQ ID NO: 7 or SEQ ID NO: 8 or SEQ ID NO: 9 or SEQ ID NO: 17 or SEQ ID NO: 35 or SEQ ID NO: 37, but is not limited thereto. In this case, in the sequence having the homology or identity, the codon encoding the amino acid corresponding to the 129th position in SEQ ID NO: 1 may be one of the codons encoding glycine or alanine, the codon encoding the amino acid corresponding to the 241st position may be one of the codons encoding glutamine or threonine, the codon encoding the amino acid corresponding to the 246th position may be one of the codons encoding valine, and the codon encoding the amino acid corresponding to the 330th position may be one of the codons encoding isoleucine.

The polynucleotide of the present disclosure may include, without limitation, a probe that can be constructed from a known gene sequence, for example, a sequence as long as the sequence can hybridize with a sequence complementary to all or part of the polynucleotide sequence of the present disclosure under a stringent condition. The "stringent condition" means a condition that enables specific hybridization between polynucleotides. Such a condition is specifically described in literatures (see J. Sambrook et al., Molecular Cloning, A Laboratory Manual, 2nd Edition, Cold Spring Harbor Laboratory press, Cold Spring Harbor, New York, 1989; and F. M. Ausubel et al., Current Protocols in Molecular Biology, John Wiley & Sons, Inc., New York, 9.50-9.51, 11.7-11.8). For example, a condition in which polynucleotides having high homology or identity, namely polynucleotides having 70% or more, 75% or more, 80% or more, 85% or more, 90% or more, 95% or more, 96% or more, 97% or more, 98% or more, or 99% or more homology or identity hybridize with each other and polynucleotides having homology or identity lower than this do not hybridize with each other; or a condition in which washing is performed one time, specifically two to three times at salt concentration and temperature equivalent to 60° C., 1×SSC, 0.1% SDS, which are washing conditions of ordinary southern hybridization, specifically 60° C., 0.1×SSC, 0.1% SDS, more specifically 68° C., 0.1×SSC, 0.1% SDS may be exemplified.

Hybridization requires that two nucleic acids have complementary sequences although mismatch between bases is possible depending on the stringency of hybridization. The term "complementary" is used to describe the relation between nucleotide bases capable of hybridizing with each other. For example, with regard to DNA, adenine is complementary to thymine and cytosine is complementary to guanine. Hence, the polynucleotide of the present disclosure may also include substantially similar nucleic acid sequences as well as isolated nucleic acid fragments complementary to the overall sequence.

Specifically, a polynucleotide having homology or identity to the polynucleotide of the present disclosure may be detected using hybridization conditions including a hybridization step at a Tm value of 55° C. under the above-described conditions. The Tm value may be 60° C., 63° C. or 65° C., but is not limited thereto, and may be appropriately adjusted by those skilled in the art depending on the purpose.

The appropriate stringency for hybridizing polynucleotides depends on the length of the polynucleotides and the degree of complementarity, and the parameters are well known in the art (for example, J. Sambrook et al., supra).

Still another aspect of the present disclosure is to provide a vector comprising the polynucleotide of the present disclosure.

The vector may be an expression vector for expressing the polynucleotide in a host cell, but is not limited thereto.

The vector of the present disclosure may contain a DNA preparation including a nucleotide sequence of a polynucleotide encoding the target polypeptide operably linked to a suitable expression control region (or expression control sequence) so that the target polypeptide can be expressed in a suitable host. The expression control region may contain a promoter capable of initiating transcription, an arbitrary operator sequence for regulating such transcription, a sequence encoding a suitable mRNA ribosome binding site, and a sequence controlling the termination of transcription and translation. After being transformed into a proper host cell, the vector may be replicated or function independently of the host genome, and may be integrated into the genome itself.

The vector used in the present disclosure is not particularly limited, and an arbitrary vector known in the art may be used. Examples of commonly used vectors include plasmids, cosmids, viruses, and bacteriophages in a natural or recombinant state. For example, pWE15, M13, MBL3, MBL4, IXII, ASHII, APII, t10, t11, Charon4A, and Charon21A may be used as a phage vector or cosmid vector, and pDZ-, pBR-, pUC-, pBluescript II-, pGEM-, pTZ-, pCL-, pSK-, pSKH-, pET-based vectors, and the like may be used as a plasmid vector. Specifically, pDZ, pDC, pDCM2, pACYC177, pACYC184, pCL, pSK, pSKH130, pECCG117, pUC19, pBR322, pMW118, pCC1BAC vectors, and the like may be used.

As an example, a polynucleotide encoding a target polypeptide may be inserted into a chromosome through a vector for insertion into intracellular chromosome. The insertion of a polynucleotide into a chromosome may be performed by an arbitrary method known in the art, for example, homologous recombination, but is not limited thereto. The vector may further include a selection marker for confirming the insertion into a chromosome. The selection marker is used to select cells transformed with the vector, that is, to confirm the insertion of a target nucleic acid molecule, and markers that confer selectable phenotypes such as drug resistance, auxotrophy, resistance to cytotoxic agents, or expression of surface polypeptides may be used. In an environment treated with a selective agent, only cells expressing a selection marker survive or exhibit other expression traits, and thus transformed cells can be selected.

As used herein, the term "transformation" means introducing a vector including a polynucleotide encoding a target polypeptide into a host cell or microorganism so that the polypeptide encoded by the polynucleotide can be expressed in the host cell. The transformed polynucleotide may include all polynucleotides regardless of whether they are inserted and located into the chromosome of the host cell or located outside the chromosome as long as they can be expressed in the host cell. The polynucleotide includes DNA and/or RNA encoding a target polypeptide. The polynucleotide may be introduced in any form as long as it can be introduced into and expressed in a host cell. For example, the polynucleotide may be introduced into a host cell in the form of an expression cassette, which is a gene construct containing all elements necessary for self-expression. The expression cassette may usually contain a promoter operably linked to the polynucleotide, a transcription termination signal, a ribosome binding site, and a translation termination signal. The expression cassette may be in the form of an expression vector capable of self-replication. The polynucleotide may be introduced into a host cell in its own form and operably linked to a sequence necessary for expression in the host cell, but is not limited thereto.

As used herein, the term "operably linked" means that a promoter sequence, that initiates and mediates transcription of a polynucleotide encoding the target variant of the present disclosure, and the polynucleotide sequence are functionally linked to each other.

Still another aspect of the present disclosure is to provide a microorganism of the genus Escherichia, comprising the variant of the present disclosure or a polynucleotide encoding the variant.

The microorganism of the present disclosure may contain the mutant polypeptide of the present disclosure, a polynucleotide encoding the polypeptide, or a vector including the polynucleotide of the present disclosure.

As used herein, the term "strain (or microorganism)", which includes both wild-type microorganisms and microorganisms in which genetic modification has occurred naturally or artificially, refers to a microorganism in which a specific mechanism is weakened or enhanced due to causes such as insertion of an exogenous gene or enhancement or inactivation of the activity of an endogenous gene, and may be a microorganism containing genetic modification for the production of a desired polypeptide, protein, or product.

The microorganism of the present disclosure may be a microorganism containing any one or more of the variant of the present disclosure, the polynucleotide of the present disclosure, and a vector including the polynucleotide of the present disclosure; a microorganism modified to express the variant of the present disclosure or the polynucleotide of the present disclosure; a microorganism (for example, a recombinant microorganism) expressing the variant of the present disclosure or the polynucleotide of the present disclosure; or a microorganism (for example, a recombinant microorganism) having the activity of the variant of the present disclosure, but is not limited thereto.

The microorganism of the present disclosure may be a microorganism having the O-phosphoserine producing ability.

The microorganism of the present disclosure may be a microorganism naturally having the YhhS or O-phosphoserine producing ability or a microorganism in which the variant of the present disclosure or a polynucleotide encoding the variant (or a vector including the polynucleotide) is introduced into and/or the O-phosphoserine producing ability is imparted to a parent strain without the YhhS or O-phosphoserine producing ability, but is not limited thereto.

As an example, the strain of the present disclosure is a cell or microorganism that is transformed with a vector including the polynucleotide of the present disclosure or a polynucleotide encoding the variant of the present disclosure and expresses the variant of the present disclosure. For the purpose of the present disclosure, the strain of the present disclosure may include all of the microorganisms capable of producing O-phosphoserine by containing the variant of the present disclosure. For example, the strain of the present disclosure may be a recombinant strain, which expresses the YhhS variant by introducing a polynucleotide encoding the variant of the present disclosure into a natural wild-type microorganism or a microorganism producing O-phosphoserine and has increased O-phosphoserine producing ability. The recombinant strain having increased O-phosphoserine producing ability may be a microorganism having increased O-phosphoserine producing ability compared to a natural wild-type microorganism, a YhhS-unmodified microorganism (namely, a microorganism expressing wild-type YhhS (SEQ ID NO: 1)), or a microorganism not expressing a mutant YhhS (SEQ ID NO: 2 or SEQ ID NO: 3 or SEQ ID NO: 4 or SEQ ID NO: 5 or SEQ ID NO: 12 or SEQ ID NO: 34 or SEQ ID NO: 36), but is not limited thereto. For example, the wild-type YhhS-introduced microorganism, which is the target strain for comparing the increase in O-phosphoserine producing ability, may be CA07-0012 (KCCM 11121P, Korean Patent No. 10-1381048 and US Patent Application Publication No. 10-2012-0190081), which is a microorganism in which the SerB activity is weakened compared to intrinsic activity, but is not limited thereto.

As an example, the recombinant strain having increased production ability may have O-phosphoserine producing ability increased by about 1% or more, specifically, about 1% or more, about 10% or more, about 20% or more, about 29% or more, about 30% or more, about 40% or more, about 50% or more, about 60% or more, about 70% or more, about 80% or more, about 90% or more, about 100% or more, about 110% or more, about 120% or more, about 130% or more, about 140% or more, about 144% or more, about 150% or more, about 160% or more, about 170% or more, about 180% or more, about 190% or more, about 200% or more, about 210% or more, about 220% or more, about 230% or more, about 233% or more, about 240% or more, about 250% or more, about 252% or more, about 260% or more, about 267% or more, about 270% or more, about 280% or more, about 290% or more, about 300% or more, about 310% or more, about 320% or more, about 330% or more, or about 338% or more (the upper limit is not particularly limited, and may be, for example, about 300% or less, about 200% or less, about 100% or less, about 50% or less, about 40% or less, about 30% or less, about 20% or less, or about 15% or less) compared to the O-phosphoserine producing ability of the parent strain before mutation or unmodified microorganism, but is not limited thereto as long as it has an increased amount of + value compared to the O-phosphoserine producing ability of the parent strain before mutation or unmodified microorganism. In another example, the recombinant strain having increased production ability may have IMP-producing ability increased by about 1.01 times or more, about 1.1 times or more, about 1.2 times or more, about 1.29 times or more, about 1.3 times or more, about 1.4 times or more, about 1.5 times or more, about 1.6 times or more, about 1.7 times or more, about 1.8 times or more, about 1.9 times or more, about 2.0 times or more, about 2.1 times or more, about 2.2 times or more, about 2.3 times or more, about 2.4 times or more, about 2.44 times or more, about 2.5 times or more, about 2.6 times or more, about 2.7 times or more, about 2.8 times or more, about 2.9 times or more, about 3.0 times or more, about 3.1 times or more, about 3.2 times or more, about 3.3 times or more, about 3.33 times or more, about 3.4 times or more, about 3.5 times or more, about 3.52 times or more, about 3.6 times or more, about 3.67 times or more, about 3.7 times or more, about 3.8 times or more, about 3.9 times or more, about 4.0 times or more, about 4.1 times or more, about 4.2 times or more, about 4.3 times or more, or about 4.38 times or more (the upper limit is not particularly limited, and may be, for example, about 10 times or less, about 5 times or less, about 3 times or less, or about 2 times or less) compared to that of the parent strain before mutation or unmodified microorganism, but is not limited thereto.

As used herein, the term "unmodified microorganism" does not exclude strains containing mutations that may occur naturally in microorganisms, and may refer to a wild-type strain or native strain itself, or a strain before the trait is changed due to genetic mutation caused by natural or artificial factors. For example, the unmodified microorganism may refer to a strain in which the YhhS variant described herein is not introduced or is not yet introduced. The "unmodified microorganism" may be used interchangeably with "strain before modification", "microorganism before modification", "unmutated strain", "unmodified strain", "unmutated microorganism" or "reference microorganism".

As another example of the present disclosure, the microorganism of the present disclosure may be a microorganism capable of producing O-phosphoserine, and the kind of microorganism is not particularly limited. The microorganism of the present disclosure may possibly be either a prokaryotic cell or a eukaryotic cell, but may specifically be a prokaryotic cell. The prokaryotic cell may include, for example, microbial strains belonging to the genus *Escherichia*, genus *Erwinia*, genus *Serratia*, genus *Providencia*, genus *Corynebacterium*, and genus *Brevibacterium*, and may be specifically a microorganism of the genus *Escherichia*, more specifically *Escherichia coli*, but is not limited thereto. In particular, the microorganism of the genus *Escherichia* of the present disclosure can produce OPS and L-serine through SerA, SerC and SerB, which are enzymes in the biosynthesis pathway of L-serine (Ahmed Zahoor, *Computational and Structural Biotechnology Journal*, vol 3, 2012 October; Wendisch V F et al., *Curr Opin Microbiol.* 2006 June; 9(3):268-74; and Peters-Wendisch P et al., *Appl Environ Microbiol.* 2005 November; 7 1(II): 7 139-44).

The O-phosphoserine-producing microorganism of the present disclosure may additionally have weakened activity of phosphoserine phosphatase (SerB) compared to the intrinsic activity.

SerB of the present disclosure exhibits activity to convert O-phosphoserine into L-serine, and thus a microorganism mutated so that the SerB activity is weakened has a feature of accumulating O-phosphoserine and may be usefully used in the production of O-phosphoserine. SerB of the present disclosure may be a protein having or including the amino acid sequence set forth in SEQ ID NO: 10 or a protein consisting of or consisting essentially of the amino acid sequence set forth in SEQ ID NO: 10, but is not limited thereto. SerB of the present disclosure may have or include an amino acid sequence having at least 70%, 80%, 90%, 95% or 99% or more homology or identity to the amino acid sequence set forth in SEQ ID NO: 10 as long as it exhibits SerB activity. SerB of the present disclosure may consist of or consist essentially of an amino acid sequence having at least 70%, 80%, 90%, 95% or 99% or more homology or identity to the amino acid sequence set forth in SEQ ID NO: 10, but is not limited thereto. A polynucleotide encoding the SerB may have or include a nucleotide sequence encoding the amino acid sequence set forth in SEQ ID NO: 10. In addition, a polynucleotide encoding the SerB may consist of or consist essentially of a nucleotide sequence encoding the amino acid sequence set forth in SEQ ID NO: 10. In the polynucleotide encoding SerB of the present disclosure, various modifications may be made to the coding region within the range in which the amino acid sequence of the SerB protein is not changed due to the degeneracy of codons or in consideration of the codons preferred in the organism to express the SerB protein. The polynucleotide encoding the SerB of the present disclosure may have or include a nucleotide sequence having at least 70%, 80%, 90%, 95% or 99% or more and less than 100% homology or identity to the nucleotide sequence of SEQ ID NO: 11. The polynucleotide encoding the SerB of the present disclosure may consist of or consist essentially of a nucleotide sequence having at least 70%, 80%, 90%, 95% or 99% or more and less than 100% homology or identity to the nucleotide sequence of SEQ ID NO: 11, but is not limited thereto.

As used herein, the term "weakening" of a polypeptide is a concept including both a case of having decreased activity compared to the intrinsic activity or a case of not exhibiting activity. The weakening may be used interchangeably with terms such as inactivation, deficiency, down-regulation, decrease, reduction, and attenuation.

The weakening may also include a case where the activity of the polypeptide itself is decreased or eliminated compared to the activity of the polypeptide originally possessed by a microorganism due to mutation of the polynucleotide encoding the polypeptide, and the like; a case where the overall activity degree and/or concentration (expression level) of the polypeptide in a cell is lower than that of the native strain due to inhibition of gene expression of the polynucleotide encoding the polypeptide or inhibition of translation into the polypeptide, and the like; a case where a polynucleotide is not expressed at all, and/or a case where the polypeptide does not exhibit activity even though the polynucleotide is expressed. The "intrinsic activity" refers to the activity of a specific polypeptide originally possessed by the parent strain before transformation or the wild-type or unmodified microorganism when a trait is changed due to genetic mutation caused by natural or artificial factors. The intrinsic activity may be used interchangeably with "activity before modification". The "inactivation, deficiency, decrease, down-regulation, reduction, attenuation" of the activity of a polypeptide compared to the intrinsic activity means that the activity of a polypeptide is lowered compared to the activity of a specific polypeptide originally possessed by the parent strain before transformation or unmodified microorganism.

Weakening of the activity of a polypeptide may be performed by an arbitrary method known in the art, but is not limited thereto, and may be achieved by application of various methods well known in the art (for example, Nakashima N et al., Bacterial cellular engineering by genome editing and gene silencing. *Int J Mol Sci.* 2014; 15(2):2773-2793, Sambrook et al. *Molecular Cloning* 2012, and the like). Specifically, weakening of a polypeptide of the present disclosure may be:

1) deletion of all or part of a gene encoding a polypeptide;
2) modification of an expression control region (or expression control sequence) to decrease the expression of a gene encoding a polypeptide;
3) modification of an amino acid sequence constituting a polypeptide so that the activity of the polypeptide is eliminated or weakened (for example, deletion/substitution/addition of one or more amino acids in the amino acid sequence);
4) modification of a gene sequence encoding a polypeptide so that the activity of the polypeptide is eliminated or weakened (for example, deletion/substitution/addition of one or more nucleotides in a nucleotide sequence of a polypeptide gene to encode the polypeptide modified to eliminate or weaken the activity of the polypeptide);
5) modification of a nucleotide sequence encoding a start codon or 5'-UTR region of a gene transcript encoding a polypeptide;
6) introduction of an antisense oligonucleotide (for example, antisense RNA) that complementarily binds to a transcript of a gene encoding a polypeptide;
7) addition of a sequence complementary to the Shine-Dalgarno sequence to front of the Shine-Dalgarno sequence of a gene encoding a polypeptide to form a secondary structure to which ribosomes cannot be attached;
8) addition of a promoter transcribed in the opposite direction to the 3' end of an open reading frame (ORF) of a gene sequence encoding a polypeptide (reverse transcription engineering, RTE); or
9) combination of two or more selected from 1) to 8) above, but is not particularly limited thereto.

For example,

1) The deletion of a part or all of the gene encoding a polypeptide may be elimination of the entire polynucleotide encoding the endogenous target polypeptide in the chromosome, replacement with a polynucleotide in which some nucleotides are deleted, or replacement with a marker gene.
2) The modification of an expression control region (or expression control sequence) may be occurrence of a mutation in the expression control region (or expression control sequence) by deletion, insertion, non-conservative or conservative substitution, or a combination thereof, or replacement with a sequence exhibiting far weaker activity. The expression control region contains, but is not limited to, a promoter, an operator sequence, a sequence encoding a ribosome binding site, and a sequence regulating the termination of transcription and translation.

The modification of an amino acid sequence or polynucleotide sequence of 3) or 4) may be occurrence of a mutation in the amino acid sequence of the polypeptide or the polynucleotide sequence encoding the polypeptide by deletion, insertion, non-conservative or conservative substitution, or a combination thereof so that the activity of the polypeptide is weakened, or replacement with an amino acid sequence or polynucleotide sequence modified to exhibit far weaker activity or an amino acid sequence or polynucleotide sequence modified not to exhibit activity, but is not limited thereto. For example, the expression of a gene may be inhibited or weakened by introducing a mutation into the polynucleotide sequence and thus forming a termination codon, but is not limited thereto.

5) The modification of a nucleotide sequence encoding a start codon or 5'-UTR region of a gene transcript encoding a polypeptide may be, for example, but is not limited to, substitution with a nucleotide sequence encoding another start codon having a lower polypeptide expression rate compared to that of the endogenous start codon.
6) The introduction of an antisense oligonucleotide (for example, antisense RNA) that complementarily binds to a transcript of a gene encoding a polypeptide may refer to, for example, literatures [Weintraub, H. et al., Antisense-RNA as a molecular tool for genetic analysis, Reviews—*Trends in Genetics, Vol.* 1(1) 1986].
7) The addition of a sequence complementary to the Shine-Dalgarno sequence to front of the Shine-Dalgarno sequence of a gene encoding a polypeptide to form a secondary structure to which ribosomes cannot be attached may be to render mRNA translation impossible or reduce the mRNA translation rate.
8) In addition, the addition of a promoter transcribed in the opposite direction to the 3' end of an open reading frame (ORF) of a gene sequence encoding the polypeptide (reverse transcription engineering, RTE) may be to form an antisense nucleotide complementary to the transcript of the gene encoding a polypeptide and thus weaken the activity.

As used herein, the term "enhancement" of polypeptide activity means that the activity of the polypeptide is increased compared to the intrinsic activity. The enhancement may be used interchangeably with terms such as activation, up-regulation, overexpression, and increase. Here, activation, enhancement, up-regulation, overexpression, and increase may include both exhibiting activity that has not been originally possessed and exhibiting improved activity compared to the intrinsic activity or the activity before modification. The "intrinsic activity" refers to the activity of a specific polypeptide originally possessed by the parent strain before transformation or unmodified microorganism when a trait is changed due to genetic mutation caused by natural or artificial factors. The "intrinsic activity" may be used interchangeably with "activity before modification". The "enhancement", "up-regulation", "overexpression", or "increase" of the activity of a polypeptide compared to the intrinsic activity means that the activity of a polypeptide is improved compared to the activity and/or concentration (expression level) of a specific polypeptide originally possessed by the parent strain before transformation or unmodified microorganism.

The enhancement may be achieved by introducing a foreign polypeptide or enhancing the activity and/or concentration (expression level) of the endogenous polypeptide. The enhancement of the polypeptide activity may be confirmed from the increase in the activity degree, expression level of the polypeptide or the amount of product excreted from the polypeptide.

The enhancement of the polypeptide activity is not limited as long as the activity of the target polypeptide can be enhanced compared to that of the microorganism before modification, and various methods well known in the art can be applied. Specifically, the enhancement may be achieved by genetic engineering and/or protein engineering well known to those skilled in the art, which are routine methods of molecular biology, but is not limited thereto (for example, Sitnicka et al. Functional Analysis of Genes. *Advances in Cell Biology*. 2010, Vol. 2. 1-16, Sambrook et al. Molecular Cloning 2012, and the like). Specifically, the enrichment of a polypeptide of the present disclosure may be 1) an increase in the intracellular copy number of a polynucleotide encoding a polypeptide;
2) modification of a gene expression control region in a chromosome encoding a polypeptide (for example, occurrence of a mutation in an expression control region, replacement with a sequence exhibiting far stronger activity, or insertion of a sequence exhibiting far stronger activity);
3) modification of a nucleotide sequence encoding a start codon or 5'-UTR region of a gene transcript encoding a polypeptide;
4) modification of an amino acid sequence of a polypeptide to enhance polypeptide activity;
5) modification of a polynucleotide sequence encoding a polypeptide to enhance the polypeptide activity (for example, modification of the polynucleotide sequence of a polypeptide gene to encode the polypeptide modified to enhance the polypeptide activity);
6) introduction of a foreign polypeptide exhibiting the activity of a polypeptide or a foreign polynucleotide encoding the polypeptide;
7) codon optimization of a polynucleotide encoding a polypeptide;
8) analysis of the tertiary structure of a polypeptide to select an exposed site and modify or chemically modify the exposed site; or
9) combination of two or more selected from 1) to 8) above, but is not particularly limited thereto.

More specifically, 1) the increase in the intracellular copy number of a polynucleotide encoding a polypeptide may be achieved by introduction into a host cell of a vector capable of being replicated and functioning independently of a host to which a polynucleotide encoding the corresponding polypeptide is operably linked. Alternatively, the increase may be achieved by introducing one copy or two or more copies of a polynucleotide encoding the polypeptide into a chromosome in a host cell. The introduction into a chromosome may be performed by introducing a vector capable of inserting the polynucleotide into a chromosome in a host cell into the host cell, but is not limited thereto. The vector is as described above.
2) the replacement of a gene expression control region (or expression control sequence) in a chromosome encoding a polypeptide with a sequence having strong activity may be, for example, a replacement of the gene expression control region with a sequence, in which a mutation has occurred in the sequence by deletion, insertion, non-conservative or conservative substitution, or a combination thereof, or a sequence having stronger activity, so as to further enhance the activity of the expression control region. The expression control region may contain, but is not particularly limited to, a promoter, an operator sequence, a sequence encoding a ribosome binding site, and a sequence controlling the termination of transcription and translation. As an example, the replacement may be replacement of the original promoter with a strong promoter, but is not limited thereto.

Examples of known strong promoters include, but are not limited to, CJ1 to CJ7 promoters (U.S. Pat. No. 7,662,943 B2), lac promoter, trp promoter, trc promoter, tac promoter, lambda phage PR promoter, PL promoter, tet promoter, gapA promoter, SPL7 promoter, SPL13 (sm3) promoter (U.S. Pat. No. 10,584,338 B2), O2 promoter (U.S. Pat. No. 10,273,491 B2), tkt promoter, and yccA promoter.

3) the modification of a nucleotide sequence encoding a start codon or 5'-UTR region of a gene transcript encoding a polypeptide may be, for example, but not limited to, substitution with a nucleotide sequence encoding another start codon having a higher polypeptide expression rate than the endogenous start codon.

The modification of an amino acid sequence or polynucleotide sequence of 4) or 5) may be occurrence of a mutation in the amino acid sequence of the polypeptide or the polynucleotide sequence encoding the polypeptide by deletion, insertion, non-conservative or conservative substitution, or a combination thereof so that the activity of the polypeptide is enhanced, or replacement with an amino acid sequence or polynucleotide sequence modified to exhibit far stronger activity or an amino acid sequence or polynucleotide sequence modified to exhibit increased activity, but is not limited thereto. The replacement may be specifically performed by inserting a polynucleotide into a chromosome by homologous recombination, but is not limited thereto. In this case, the vector used may further include a selection marker for confirming the insertion into a chromosome. The selection marker is as described above.

6) the introduction of a foreign polynucleotide exhibiting the activity of a polypeptide may be introduction of a foreign polynucleotide encoding a polypeptide, which exhibits activity the same as/similar to that of the polypeptide, into a host cell. The foreign polynucleotide is not limited in its origin or sequence as long as it exhibits activity the same as/similar to that of the polypeptide. The introduction may be performed by appropriately selecting known transformation methods by those skilled in the art. As the introduced polynucleotide is expressed in the host cell, a polypeptide may be produced and its activity may be increased.
7) the codon optimization of a polynucleotide encoding a polypeptide may be codon optimization of an endogenous polynucleotide to increase transcription or translation in a host cell, or codon optimization of a foreign polynucleotide so that optimized transcription and translation is performed in a host cell.
8) the analysis of the tertiary structure of a polypeptide to select an exposed site and modify or chemically modify the exposed site may be, for example, to determine a template protein candidate according to the degree of sequence similarity by comparing sequence information of a polypeptide to be analyzed with a database in which sequence information of known proteins is stored, confirm the structure based on this, select an exposed site to be modified or chemically modified, and qualify the exposed site.

Such enhancement of the polypeptide activity may be an increase in the activity or concentration expression level of the corresponding polypeptide based on the activity or concentration of the polypeptide expressed in the wild-type microbial strain or microbial strain before modification, or an increase in the amount of a product being produced from the polypeptide, but is not limited thereto.

Modification of part or all of the polynucleotide in the microorganism of the present disclosure may be induced by (a) homologous recombination using a vector for chromosome insertion into microorganisms or genome editing using engineered nuclease (e.g., CRISPR-Cas9) and/or (b) light such as ultraviolet rays and radiation and/or treatment with chemicals, but is not limited thereto. The method for modifying part or all of the gene may include a method by DNA recombination technology. For example, by injecting a nucleotide sequence or vector including a nucleotide sequence homologous to the target gene into the microorganism to cause homologous recombination, deletion of part or all of a gene may be achieved. The injected nucleotide sequence or vector may include a dominant selection marker, but is not limited thereto.

The microorganism may be a microorganism having further decreased ability of OPS to enter and degrade cells.

As for the contents of OPS-producing microorganisms as described above, in addition to the contents described above, the contents disclosed in U.S. Pat. No. 8,557,549 B2 or US Patent Application Publication No. 2012-0190081 or the like may be used as reference materials of the present disclosure, but the contents are not limited thereto.

In the microorganism of the present disclosure, "variant", "polynucleotide", "O-phosphoserine", and the like are as described in the other aspects above.

Still another aspect of the present disclosure is to provide a method for producing O-phosphoserine, which comprises culturing a microorganism containing the variant of the present disclosure or a polynucleotide encoding the variant in a medium.

The method for producing O-phosphoserine of the present disclosure may include a step of culturing a microorganism containing the variant of the present disclosure or a polynucleotide encoding the variant in a medium.

As used herein, the term "culturing" means growing the microorganism of the present disclosure under properly controlled environmental conditions. The culturing process of the present disclosure may be performed in a suitable medium known in the art under suitable culturing conditions known in the art. Such a culturing process may be easily adjusted and used by those skilled in the art depending on the selected strain. Specifically, the culturing may be batch culturing, continuous culturing, and fed-batch culturing, but is not limited thereto.

As used herein, the term "medium" refers to a material in which nutrients required for culturing the microorganism of the present disclosure are mixed as a main component, and supplies nutrients, growth factors, and the like including water, which are essential for survival and growth. Specifically, as the medium and other culturing conditions used for culturing the microorganism of the present disclosure, any medium may be used without particular limitation as long as it is used for culturing ordinary microorganisms, but the microorganism of the present disclosure may be cultured in an ordinary medium containing proper carbon sources, nitrogen sources, phosphorus sources, inorganic compounds, amino acids, and/or vitamins, etc. under an aerobic condition while the temperature, pH, and the like are controlled.

The carbon sources in the present disclosure include carbohydrates such as glucose, saccharose, lactose, fructose, sucrose, and maltose; sugar alcohols such as mannitol and sorbitol; organic acids such as pyruvic acid, lactic acid, and citric acid; amino acids such as glutamic acid, methionine, and lysine; and the like. Natural organic nutrients such as starch hydrolysates, molasses, blackstrap molasses, rice bran, cassava, sugarcane bagasse, and corn steep liquor may be used. Specifically, carbohydrates such as glucose and sterilized pre-treated molasses (namely, molasses converted into reducing sugar) may be used, and appropriate amounts of other carbon sources may be variously used without limitation. These carbon sources may be used singly or in combination of two or more, but the carbon sources are not limited thereto.

As the nitrogen sources, inorganic nitrogen sources such as ammonia, ammonium sulfate, ammonium chloride, ammonium acetate, ammonium phosphate, ammonium carbonate, and ammonium nitrate; and organic nitrogen sources such as amino acids such as glutamic acid, methionine, and glutamine, peptone, NZ-amine, meat extract, yeast extract, malt extract, corn steep liquor, casein hydrolysates, fish or decomposition products thereof, and defatted soybean cake or decomposition products thereof may be used. These nitrogen sources may be used singly or in combination of two or more, but the nitrogen sources are not limited thereto.

The phosphorus sources may include potassium phosphate monobasic and potassium phosphate dibasic or sodium phosphate monobasic and sodium phosphate dibasic. As the inorganic compounds, sodium chloride, calcium chloride, iron chloride, magnesium sulfate, iron sulfate, manganese sulfate, calcium carbonate, and the like may be used. In addition to these, amino acids, vitamins and/or appropriate precursors may be contained in the medium. These components or precursors may be added to the medium either batchwise or continuously. However, the medium is not limited thereto.

The medium may contain a metal salt such as magnesium sulfate or iron sulfate, and in addition, amino acids, vitamins and appropriate precursors. These media or precursors may be added to the culture batchwise or continuously, but are not limited thereto.

As an example, in the culturing of a recombinant microorganism in which SerB activity is weakened compared to the intrinsic activity, glycine or serine may be additionally contained in the medium since the serine requirement of the microorganism is induced. Glycine may be provided in the form of purified glycine, yeast extract containing glycine, and tryptone, and the concentration of glycine contained in the culturing medium may be usually 0.1 g/L to 10 g/L, specifically 0.5 g/L to 3 g/L. Serine may be provided in the form of purified serine, yeast extract containing serine, and tryptone, and the concentration of serine contained in the culturing medium may be usually 0.1 g/L to 5 g/L, specifically 0.1 g/L to 1 g/L.

During culturing of the microorganism of the present disclosure, compounds such as ammonium hydroxide, potassium hydroxide, ammonia, phosphoric acid, and sulfuric acid may be added to the medium in an appropriate manner to adjust the pH of the medium. During culturing, an antifoaming agent such as fatty acid polyglycol ester may be used to suppress bubble formation. Oxygen or oxygen-containing gas may be injected into the medium in order to maintain the aerobic state of the medium, or gas may not be injected or nitrogen, hydrogen or carbon dioxide gas may be injected in order to maintain anaerobic and microaerobic states, but the culturing conditions are not limited thereto.

In the culturing of the present disclosure, the culturing temperature may be maintained at 20° C. to 45° C., specifically 25° C. to 40° C., and the culturing may be performed for about 10 to 160 hours, but the culturing conditions are not limited thereto.

O-phosphoserine produced by the culturing of the present disclosure may be secreted into the medium or remain in the cells.

The method for producing O-phosphoserine of the present disclosure may further include a step of preparing the microorganism of the present disclosure, a step of preparing a medium for culturing the microorganism, or a combination thereof (in any order), for example, prior to the culturing step.

The method for producing O-phosphoserine of the present disclosure may further include a step of recovering O-phosphoserine from the medium after culturing (the medium which has undergone culturing) or microorganism. The recovering step may be further included after the culturing step.

The recovery may be to collect the desired O-phosphoserine using a suitable method known in the art according to the method for culturing a microorganism of the present disclosure, for example, batch, continuous, or fed-batch culturing method, and the like. For example, centrifugation, filtration, treatment with a crystallized protein precipitating agent (salting-out method), extraction, sonication, ultrafiltration, dialysis, various kinds of chromatography such as molecular sieve chromatography (gel filtration), adsorption chromatography, ion exchange chromatography, and affinity chromatography, HPLC or a combination of these methods may be used. The desired O-phosphoserine may be recovered from the medium or microorganism using a suitable method known in the art.

The method for producing O-phosphoserine of the present disclosure may further include a purification step. The purification may be performed by a suitable method known in the art. In an example, when the method for producing O-phosphoserine of the present disclosure includes both a recovery step and a purification step, the recovery step and the purification step may be performed continuously or discontinuously in any order, or may be performed simultaneously or as one integrated step, but are not limited thereto.

In the method of the present disclosure, "variant", "polynucleotide", "vector", "microorganism", and the like are as described in the other aspects above.

Still another aspect of the present disclosure is to provide a method for producing cysteine or a derivative of cysteine, which comprises a) culturing an O-phosphoserine-producing microorganism containing the variant of the present disclosure or a polynucleotide encoding the variant in a medium to produce O-phosphoserine or a O-phosphoserine-containing medium; and b) bringing O-phosphoserine sulfhydrylase (OPSS) or a microorganism expressing O-phosphoserine sulfhydrylase, the O-phosphoserine or O-phosphoserine-containing medium produced in the step a), and a sulfide into contact with one another.

Specifically, the method may be a method for producing cysteine or a derivative cysteine, which includes a step of culturing an O-phosphoserine-producing microorganism containing any one or more selected from a polypeptide including the amino acid sequence of SEQ ID NO: 2 or SEQ ID NO: 3 or SEQ ID NO: 4 or SEQ ID NO: 5 or SEQ ID NO: 12 or SEQ ID NO: 34 or SEQ ID NO: 36 while exhibiting O-phosphoserine exporting activity; a polypeptide including an amino acid sequence having at least 90%, 91%, 92%, 93%, 94%, 95%, 96%, 97%, 98%, 99%, 99.5%, 99.7%, or 99.9% or more homology or identity to this polypeptide; a mutant polypeptide having an amino acid sequence in which some sequences are deleted, modified, substituted, or added while the mutation of amino acids corresponding to the i) 129th position; ii) 241st position; iii) 129th position and 241st position; iv) 241st position, 246th position and 330th position; and v) 129th position, 241st position, 246th position, and 330th position in the amino acid sequence of SEQ ID NO: 1 is fixed; a polynucleotide encoding the variant of the present disclosure; or a vector including a polynucleotide encoding the variant of the present disclosure in a medium to produce O-phosphoserine or a O-phosphoserine-containing medium; and a step of reacting O-phosphoserine sulfhydrylase or a microorganism expressing O-phosphoserine sulfhydrylase and the O-phosphoserine or O-phosphoserine-containing medium produced in the step with a sulfide.

As used herein, the term "derivative" is a similar compound obtained by chemically changing a part of a certain compound, and usually refers to a compound in which a hydrogen atom or specific atomic group in a compound is substituted with another atom or atomic group.

As used herein, the term "a derivative of cysteine" refers to a compound in which a hydrogen atom or specific atomic group of cysteine is substituted with another atom or atomic group. For example, the cysteine derivative may be in a form in which another atom or group is attached to the nitrogen atom in an amine group (—$NH_2$) or the sulfur atom in a thiol group (—SH) of cysteine, and examples thereof include NAC (N-acetylcysteine), SCMC (S-carboxymethylcysteine), BOC-CYS (ME)-OH, (R)—S-(2-amino-2-carboxyethyl)-L-homocysteine, (R)-2-amino-3-sulfopropionic acid, D-2-amino-4-(ethylthio) butyric acid, 3-sulfino-L-alanine, Fmoc-Cys (Boc-methyl)-OH, seleno-L-cystine, S-(2-thiazolyl)-L-cysteine, S-(2-thienyl)-L-cysteine, and S-(4-tolyl)-L-cysteine, but are not limited thereto.

As long as cysteine is produced according to the method of the present disclosure, conversion of cysteine into various cysteine derivatives may be easily possible by a method well known in the art.

Specifically, the method for producing the cysteine derivative may further include a step of converting cysteine produced in the step b) into a cysteine derivative. For example, NAC (N-acetylcysteine) may be synthesized by reacting cysteine with an acetylation agent, or S-carboxymethylcysteine (SCMC) may be synthesized by reacting cysteine with haloacetic acid under a basic condition, but the conversion of cysteine into a cysteine derivative is not limited thereto.

The cysteine derivative may be used in an antitussive agent, a cough reliever, and remedial agents for bronchitis, bronchial asthma and sore throat mainly as a pharmaceutical raw material, but is not limited thereto.

As used herein, the term "O-phosphoserine sulfhydrylase (OPSS)" refers to an enzyme that catalyzes a reaction to convert O-phosphoserine into cysteine by providing a thiol group (SH group) to O-phosphoserine. The enzyme may be first discovered in *Aeropyrum pernix, Mycobacterium tuberculosis, Mycobacterium smegmatis*, and *Trichomonas vaginalis* (Mino K and Ishikawa K, FEBS letters, 551:133-138, 2003; and Burns K E et al. *J. Am. Chem. Soc.,* 127:11602-11603, 2005). The O-phosphoserine sulfhydrylase includes not only wild-type O-phosphoserine sulfhydrylase, but also variants, which have sequences in which part of the sequence of a polynucleotide encoding the O-phosphoserine sulfhydrylase is deleted, substituted, or added and exhibit activity equivalent to or higher than that of wild-type O-phosphoserine sulfhydrylase. The O-phosphoserine sulfhydrylase may also include O-phosphoserine sulfhydrylase and variants thereof disclosed in U.S. Pat. Nos. 8,557,549 B2 and 9,127,324 B2.

As the sulfide, any sulfide that is provided in the form of a liquid or gas due to differences in pH, pressure, and solubility as well as solids commonly used in the art and can be converted into a thiol group (SH group) in the form of sulfide ($S^{2-}$), thiosulfate ($S_2O_3^{2-}$), and the like may be used without limitation. Specifically, $Na_2S$, NaSH, $H_2S$, $(NH_4)_2S$, and $Na_2S_2O_3$ that provide a thiol group to O-phosphoserine may be used, but the sulfide is not limited thereto. The reaction is a reaction for producing one cysteine or cysteine derivative by providing one thiol group to one O-phosphoserine reactive group, and the amount of sulfide added for the reaction may be 0.1 to 3 times the molar concentration of O-phosphoserine, specifically 1 to 2 times, but is not limited thereto.

In the present disclosure, the method may further include a step of recovering cysteine produced through the reaction step. In this case, the desired cysteine may be isolated and purified from the reaction mixture by suitable reactions known in the art and collected.

Still another aspect of the present disclosure is to provide a composition for O-phosphoserine production, which comprises the variant of the present disclosure, a polynucleotide encoding the variant, a vector including the polynucleotide, a microorganism containing the variant of the present disclosure or a polynucleotide encoding the variant, or a combination of two or more thereof.

The composition of the present disclosure may further contain arbitrary suitable excipients commonly used in compositions for O-phosphoserine production, and such excipients may be, for example, preservatives, wetting agents, dispersing agents, suspending agents, buffers, stabilizing agents, or isotonic agents, but is not limited thereto.

In the composition of the present disclosure, "variant", "polynucleotide", "vector", "microorganism", "medium", "O-phosphoserine", and the like are as described in the other aspects above.

Still another aspect of the present disclosure is to provide use of the variant of the present disclosure, a polynucleotide encoding the variant, a vector including the polynucleotide, or a microorganism containing the variant of the present disclosure or a polynucleotide encoding the variant for production of O-phosphoserine, cysteine or a derivative of cysteine.

Still another aspect of the present disclosure is to provide use of the variant of the present disclosure for export of O-phosphoserine from a microorganism.

DETAILED DESCRIPTION OF THE INVENTION

Hereinafter, the present disclosure will be described in more detail with reference to Examples. However, the following Examples are merely preferred embodiments for illustrating the present disclosure, and therefore, the scope of the present disclosure is not intended to be limited thereto. Meanwhile, technical matters not described in this specification can be sufficiently understood and easily implemented by those skilled in the art of the present disclosure or similar technical fields.

Example 1: Selection of YhhS Variant

In order to select a YhhS variant exhibiting increased OPS exporting activity, a YhhS gene variant plasmid library was constructed. The specific process is as follows.

Random mutagenesis PCR was performed using the genomic DNA of *Escherichia coli* (*E.coli*) K12 W3110 as a template and the primer pair having the nucleotide sequences of SEQ ID NOs: 13 and 14 presented in Table 1 below. Diversity PCR Random Mutagenesis Kit (Takara) was used. For PCR, after denaturation at 94° C. for 5 minutes, denaturation at 94° C. for 30 seconds, annealing at 55° C. for 30 seconds, and polymerization at 72° C. for 1 minute were repeated 20 times, followed by polymerization at 72° C. for 5 minutes.

In order to put the mutant gene fragments constructed through such a process into the pCL1920 vector having the rhtB promoter, pCL_PrhtB was first constructed.

In order to secure the rhtB promoter fragment, PCR was performed using the genomic DNA of *E. coli* K12 W3110 as a template and SEQ ID NOs: 15 and 16. For PCR, after denaturation at 94° C. for 5 minutes, denaturation at 94° C. for 30 seconds, annealing at 55° C. for 30 seconds, and polymerization at 72° C. for 1 minute were repeated 30 times, followed by polymerization at 72° C. for 5 minutes. The rhtB promoter fragment was cloned into the pCL1920 vector (GeneBank No. AB236930) digested with EcoRI and SalI using an infusion cloning kit, and pCL_PrhtB was secured. After the secured pCL_PrhtB vector was digested with ScaI, the mutant gene fragments obtained through the PCR were cloned using an infusion cloning kit. Cloning was performed by conducting the reaction at 50° C. for 60 minutes, a pCL_PrhtB-yhhS gene mutant plasmid library was thus constructed. Thereafter, the obtained plasmid was transformed into CA07-0012 (KCCM 11121P, Korean Patent No. 10-1381048 and US Patent Application Publication No. 10-2012-0190081) by electroporation.

Among others, three strains containing variants were selected, plasmids were obtained from these, and the nucleotide sequences were analyzed through sequencing technique. As a result of sequencing, it was confirmed that the selected variants were a variant in which serine of the 129th amino acid residue in the amino acid sequence of wild-type YhhS was substituted with glycine, a variant in which isoleucine of the 241th amino acid residue was substituted with glutamine, and a variant in which isoleucine of the 241 amino acid residue was substituted with threonine, aspartic acid of the 246th amino acid residue was substituted with valine, and valine of the 330th amino acid residue was substituted with isoleucine. The three strains were named CA07-0012/pCL_PrhtB-yhhS (S129G), CA07-0012/pCL_PrhtB-yhhS (I241Q) and CA07-0012/pCL_PrhtB-yhhS (I241T/D246V/V330I), respectively. The CA07-0012/pCL_PrhtB-yhhS (I241T/D246V/V330I) strain is also commonly referred to as *Escherichia coli* CA07-0352, and was deposited with the Korean Culture Center of Microorganisms (KCCM) on May 14, 2020 under the Budapest Treaty and was given an accession number KCCM 12720P.

TABLE 1

| SEQ ID NO: | Sequence (5'→3') |
|---|---|
| 13 | GGAGTTCATCagtATGCCCGAACCCGTAGCC |
| 14 | CTGCAGGTCGAAgtTTAAGATGATGAGGCGGC |
| 15 | CGACGGCCAGTGAATTCGATGGTCGATGATTAAGACATC |
| 16 | ATGCCTGCAGGTCGAAGTACTGATGAACTCCCGGTGTGTCT |

Example 2: Construction of Vector for Expression of Additional YhhS Variant 2-1. Construction of YhhS (S129A) Variant Expressing Vector and Expression Strain In order to secure the YhhS (S129A) fragment, an upstream fragment of the YhhS (S129A) was secured through PCR using *E. coli* K12 W3110 genomic DNA as a template and SEQ ID NOs: 13 and 18, a downstream fragment of the YhhS (S129A) was secured through PCR using *E. coli* K12 W3110 genomic DNA as a template in the same manner and SEQ ID NOs: 19 and 14 presented in Table 2 below. For PCR, after denaturation at 94° C. for 5 minutes, denaturation at 94° C. for 30 seconds, annealing at 55° C. for 30 seconds, and polymerization at 72° C. for 1 minute were repeated 30 times, followed by polymerization at 72° C. for 5 minutes.

After the pCL_PrhtB vector was digested with ScaI, the secured upstream fragment of YhhS (S129A) and downstream fragment of YhhS (S129A) were cloned using an infusion cloning kit (Clontech Laboratories, Inc.). Cloning was performed by conducting the reaction at 50° C. for 60 minutes, and pCL_PrhtB-yhhS (S129A) was thus secured. The secured plasmid was transformed into CA07-0012 by electroporation to secure a strain CA07-0012/pCL_PrhtB-yhhS (S129A).

TABLE 2

| SEQ ID NO: | Sequence (5'→3') |
|---|---|
| 18 | TCCCGTTCCGGCAAAcgc TTGCCCAATCCCAAGGA |
| 19 | CTTGGGATTGGGCAAgcg TTTGCCGGAACGGGATC |

2-2. Construction of YhhS (I241Q) Variant Expressing Vector, YhhS (I241T) Variant Expressing Vector and Variant Expressing Strain In order to confirm the OPS producing ability when isoleucine of the 241th amino acid residue of YhhS secured through the library was substituted with threonine other than glutamine, a strain was constructed and evaluation was conducted.

To insert the 241th amino acid mutation of YhhS into the CA07-0012 chromosome, trc was used as a promoter and the mgsA gene position was used as the insertion site.

Specifically, pSKH130 vector (US Patent Application Publication No. 2020-0048619, SEQ ID NO: 38) was used for insertion into a chromosome. The vector includes R6K replicon, SacB (Levansucrase) gene, and kanamycin resistant gene being dependent on PI protein (pir gene), the desired strain was secured using R6K and kanamycin in the first crossover using the vector, and then the antibiotic was removed from the medium with sucrose, thereby constructing a strain.

In order to introduce a form in which the 241th amino acid residue of YhhS was substituted with other amino acids into the mgsA gene position of the strain CA07-0012, it was attempted to secure the pSKH130ΔmgsA plasmid. pSKH130ΔmgsA is a vector for deleting the mgsA ORF (open reading frame), and is a plasmid containing 5' and 3' nucleotide sequences on both sides of the ORF of mgsA.

Using the primer pairs presented in Table 3 below, 5' fragments and 3' fragments were secured, respectively. The pSKH130 vector was digested with BamHI, and then a plasmid was secured using an infusion cloning kit.

TABLE 3

| | SEQ ID NO: | Sequence (5'→3') |
|---|---|---|
| Primer pair of upstream fragment of mgsA | 20 | CCTGCCATCGGATCCGGT ATCCGTTTTTGCCACCA |
| | 21 | ACCTGTGCAATAAGTACT AATGTACATCCGTAGTT |
| Primer pair of downstream fragment of mgsA | 22 | CGGATGTACATTAGTACT TATTGCACAGGTGGCAA |
| | 23 | TGATATCGAATTCCTTCG CTGTTGGTGATGACTGG |

In order to secure the trc promoter fragment, PCR was performed using SEQ ID NOs: 24 and 25 presented in Table 4 below. In order to secure two types of variant YhhS ORFs, two types of upstream and downstream fragments of variants were secured using the primer pairs presented in Table 5, respectively. The secured two types of upstream and downstream fragments, the trc promoter fragment, and a vector in which pSKH130ΔmgsA were digested with ScaI, and an infusion cloning kit were used together to secure two types of plasmids.

In order to secure a strain in which wild-type YhhS was introduced into the mgsA position as a control, a pSKH130ΔmgsA::Ptrc-yhhS plasmid was constructed. PCR was performed using an oligonucleotide pair having SEQ ID NOs: 26 and 27 to secure the YhhS ORF, and an infusion cloning kit was used together with the trc promoter fragment and a vector in which pSKH130ΔmgsA were digested with ScaI to secure a plasmid.

TABLE 4

| SEQ ID NO: | Sequence (5'→3') |
|---|---|
| 24 | CGGATGTACATTAGTCGC TTGCTGCAACTCTCTCA |
| 25 | GATAGCTCTCCTGTGTGA AATTGTTATCCGCTCAC |

TABLE 5

| | SEQ ID NO: | Sequence (5'→3') |
|---|---|---|
| Primer pair of upstream fragment of I241Q | 26 | CACAGGAAAGATATCA TGCCCGAACCCGTAGC CGA |
| | 28 | GCCGGATTTGGCGTCA TCGCCACCTTTcagAC GCTGTTTTATGACGCT |
| Primer pair of downstream fragment of I241Q | 29 | CCAACCTTTAGCGTCA TAAAACAGCGTctgAA AGGTGGCGATGACGCC |
| | 27 | ACCTGTGCAATAAGTT TAAGATGATGAGGCGG CCT |

TABLE 5-continued

| | SEQ ID NO: | Sequence (5'→3') |
|---|---|---|
| Primer pair of upstream fragment of 1241T | 26 | CACAGGAAAGATATCATGCCCGAACCCGTAGCCGA |
| | 30 | TCATAAAACAGCGTGGTAAAGGTGGCGATGACGCC |
| Primer pair of downstream fragment of 1241T | 31 | TCATCGCCACCTTTACCACGCTGTTTTATGACGCT |
| | 27 | ACCTGTGCAATAAGTTTAAGATGATGAGGCGGCCT |

The secured plasmid was transformed into the strain CA07-0012 by electroporation. The strain in which the mutation was inserted into the chromosome by recombination (crossover) was selected from LB solid medium with kanamycin, and then subjected to the secondary recombination (replacement) in a medium with sucrose so that excision of the plasmid site from the chromosome occurred. The strain undergone the secondary recombination was subjected to PCR using SEQ ID NOs: 20 and 27 and sequencing to secure two types of strains (CA07-0012ΔmgsA::Ptrc-yhhS (I241T) and CA07-0012ΔmgsA::Ptrc-yhhS (I241Q)) in which the YhhS variant was inserted into the mgsA position of the chromosome. The strain (CA07-0012ΔmgsA::Ptrc-yhhS) into which the control was introduced was also secured by the same method.

2-3. Construction of YhhS (S129G/I241Q) Variant Expressing Vector and Expression Strain Based on the YhhS (I241Q) variant, a strain in which serine of the 129th amino acid residue was replaced with glycine was constructed. In this case, the rhtB promoter was used as a promoter.

Specifically, PCR was performed using pCL_PrhtB-yhhS (I241Q) as a template and SEQ ID NOs: 32 and 33 (PCR_129G time-point in the entire plasmid) presented in Table 6 below. The secured PCR fragment was cloned using an infusion cloning kit.

The secured plasmid was transformed into CA07-0012 by electroporation to secure strain CA07-0012/pCL_PrhtB-yhhS (S129G/I241Q).

TABLE 6

| SEQ ID NO: | Sequence 5'→3' |
|---|---|
| 32 | ATTGGGCAAgGTTTTGCCGG |
| 33 | CCGGCAAAACcTTGCCCAAT |

2-4. Construction of YhhS (S129G/I241T/D246V/V330I) Variant Expressing Vector and Expression Strain The trc promoter was used, the mgsA gene was deleted, and S129G/I241T/D246V/V330I mutation was inserted thereinto.

Specifically, in order to introduce 1241T, D246V and V330I mutations into the mgsA gene position of the strain CA07-0012, the pSKH130ΔmgsA plasmid constructed in Example 2-2 was used.

In order to construct pSKH130ΔmgsA::Ptrc-yhhS (I241T/D246V/V330I), the trc promoter fragment secured in Example 2-2 was used in the same manner. PCR was performed using SEQ ID NOs: 26 and 27 and the pCL_Ptrc-yhhS (I241T/D246V/V330I) plasmid as a template to secure the ORF fragment of the YhhS (I241T/D246V/V330I). The trc promoter fragment, yhhS453 fragment, a vector in which pSKH130ΔmgsA was digested with ScaI, and an infusion cloning kit were used together to secure a plasmid pSKH130ΔmgsA::Ptrc-yhhS (I241T/D246V/V330I).

Thereafter, PCR was performed using the pSKH130ΔmgsA::Ptrc-yhhS (I241T/D246V/V330I) as a template and SEQ ID NOs: 32 and 33 (PCR_129G time-point in the entire plasmid). For PCR, after denaturation at 94° C. for 5 minutes, denaturation at 94° C. for 30 seconds, annealing at 55° C. for 30 seconds, and polymerization at 72° C. for 7 minutes were repeated 30 times, followed by polymerization at 72° C. for 5 minutes. The secured fragment and an infusion cloning kit were used to secure a plasmid pSKH130ΔmgsA::Ptrc-yhhS (129G/I241T/D246V/V330I).

The secured plasmid was transformed into the strain CA07-0012 by electroporation. For the transformed strain, the strain introduced into the chromosome in LB solid medium with kanamycin by recombination (crossover) was selected, and then excision of the plasmid site from the chromosome occurred through secondary recombination (replacement) in medium with sucrose.

The strain undergone the secondary recombination was subjected to PCR using SEQ ID NOs: 20 and 27 and sequencing to secure two types of strains (CA07-0012/pSKH130ΔmgsA::Ptrc-yhhS (I241T/D246V/V330I) and CA07-0012/pSKH130ΔmgsA::Ptrc-yhhS (129G/I241T/D246V/V330I)) in which YhhS (I241T/D246V/V330I) or YhhS (129G/I241T/D246V/V330I) was inserted into the mgsA position of the chromosome.

Example 3: Evaluation of OPS Producing Ability of YhhS Variant-Introduced Strain The O-phosphoserine producing ability of the YhhS variant-introduced strain was evaluated using the following medium (Table 7).

Specifically, in culturing, each strain was plated on LB solid medium, and then cultured overnight in an incubator at 33° C. The strain cultured overnight in LB solid medium was inoculated into the 25 mL titer medium of Table 7 below, and then cultured for 48 hours in an incubator at 33° C. at 200 rpm, and the results are presented in Tables 8 to 11.

TABLE 7

| Component of medium | Amount prepared |
|---|---|
| Glucose | 40 g |
| $KH_2PO_4$(KP1) | 6 g |
| $(NH_4)_2SO_4$ | 17 g |
| $MgSO_4$•$7H_2O$ | 1 g |
| $MnSO_4$•$4H_2O$ | 5 mg |
| $FeSO_4$•$7H_2O$ | 10 mg |
| L-glycine | 2.5 g/L |
| Yeast extract | 3 g/L |
| $CaCO_3$ | 30 g/L |
| pH | 6.8 |

3-1: Evaluation of OPS Producing Ability of Strain Into Which 129th Amino Acid-Substituted Variant of YhhS is Introduced It has been confirmed that the rate of increase in OPS producing ability is about 252% in the case of CA07-0012/ pCL_PrhtB-yhhS (S129G), a strain into which YhhS (S129G) variant is introduced and the rate of increase in OPS producing ability is about 29% in the case of CA07-0012/pCL_PrhtB-yhhS (S129A), a strain into which YhhS (S129A) variant is introduced (Table 8).

TABLE 8

| Name of strain | OPS concentration (g/L) |
|---|---|
| CA07-0012/pCL_PrhtB-yhhS | 2.1 |
| CA07-0012/pCL_PrhtB-yhhS(S129A) | 2.7 |
| CA07-0012/pCL_PrhtB-yhhS(S129G) | 5.3 |

3-2: Evaluation of OPS Producing Ability of Strain Into Which 241st Amino Acid Residue-Substituted Variant of YhhS is Introduced The rate of increase in OPS exporting ability compared to that of CA07-0012ΔmgsA::Ptrc-yhhS, a strain into which wild-type YhhS was introduced, was examined, and as a result, it has been confirmed that the rate of increase in OPS exporting ability is about 425% in the case of CA07-0012ΔmgsA::Ptrc-yhhS (I241Q), a strain into which YhhS (I241Q) variant is introduced, the rate of increase in OPS exporting ability is about 233% in the case of CA07-0012ΔmgsA::Ptrc-yhhS (I241T), a strain into which YhhS (I241T) variant is introduced, and the rate of increase in OPS exporting ability is about 267% in the case of CA07-0012ΔmgsA::Ptrc-yhhS (I241T/D246V/V330I), a strain into which YhhS (I241T/D246V/V330I) variant is introduced (Table 9).

TABLE 9

| Name of strain | OPS concentration (g/L) |
|---|---|
| CA07-0012ΔmgsA::Ptrc-yhhS | 1.2 |
| CA07-0012ΔmgsA::Ptrc-yhhS(I241T) | 2.8 |
| CA07-0012ΔmgsA::Ptrc-yhhS(I241Q) | 5.1 |
| CA07-0012ΔmgsA::Ptrc-yhhS(I241T/D246V/V330I) | 3.2 |

3-3: Evaluation of OPS Producing Ability of Strain Into Which 129th Amino Acid Residue-Substituted and 241st Amino Acid Residue-Substituted Variant of YhhS is Introduced The rate of increase in OPS exporting ability compared to that of CA07-0012/pCL_PrhtB-yhhS, a strain into which wild-type YhhS was introduced, was examined, and as a result, it has been confirmed that the rate of increase in OPS exporting ability is about 338% in the case of CA07-0012/pCL_PrhtB-yhhS (S129G/I241Q), a strain into which a YhhS (S129G/1241Q) variant is introduced (Table 10).

TABLE 10

| Name of strain | OPS concentration (g/L) |
|---|---|
| CA07-0012/pCL_PrhtB-yhhS | 2.1 |
| CA07-0012/pCL_PrhtB-yhhS(S129G/I241Q) | 7.1 |

In addition, the rate of increase in OPS exporting ability compared to that of CA07-0012ΔmgsA::Ptrc-yhhS (I241T/D246V/V330I) was examined, and as a result, it has been confirmed that the rate of increase in OPS exporting ability is about 144% in the case of CA07-0012ΔmgsA::Ptrc-yhhS (S129G/I241T/D246V/V330I), a strain into which the YhhS (S129G/I241T/D246V/V330I) variant is introduced (Table 11).

TABLE 11

| Name of strain | OPS concentration (g/L) |
|---|---|
| CA07-0012ΔmgsA::Ptrc-yhhS(I241T/D246V/V330I) | 3.2 |
| CA07-0012ΔmgsA::Ptrc-yhhS(S129G/I241T/D246V/V330I) | 4.6 |

Based on the above description, those skilled in the art to which the present disclosure pertains will understand that the present disclosure may be implemented in other specific forms without changing the technical spirit or essential characteristics thereof. In this regard, it should be understood that the embodiments described above are illustrative in all respects and not restrictive. With regard to the scope of the present disclosure, it should be construed that all changes and modifications derived from the meaning and scope of the claims described below and their equivalents rather than the above detailed description are included in the scope of the present disclosure.

The invention claimed is:

1. A YhhS variant, wherein serine corresponding to 129th position in SEQ ID NO: 1 is substituted with glycine or alanine.

2. The YhhS variant according to claim 1, wherein isoleucine corresponding to 241st position in SEQ ID NO: 1 is substituted with glutamine.

3. The YhhS variant according to claim 1, wherein aspartic acid corresponding to 246th position in SEQ ID NO: 1 is substituted with valine.

4. A polynucleotide encoding the variant according to claim 1.

5. A microorganism of the genus *Escherichia* comprising the polynucleotide according to claim 4.

6. A method for producing O-phosphoserine, the method comprising culturing the microorganism according to claim 5.

7. A method for producing cysteine or a derivative of cysteine, the method comprising:

a) producing O-phosphoserine according to the method of claim 6; and b) contacting the O-phosphoserine with (i)O-phosphoserine sulfhydrylase (OPSS) or a microorganism expressing OPSS, and (ii) a sulfide, wherein the derivative of cysteine is selected from the group consisting of NAC (N-acetylcysteine), SCMC (S-carboxymethylcysteine), BOC-CYS(ME)-OH, (R)—S-(2-amino-2-carboxyethyl)-L-homocysteine, (R)-2-amino-3-sulfopropionic acid, D-2-amino-4-(ethylthio)butyric acid, 3-sulfino-L-alanine, Fmoc-Cys (Boc-methyl)-OH, seleno-L-cystine, S-(2-thiazolyl)-L-cysteine, S-(2-thienyl)-L-cysteine, and S-(4-tolyl)-L-cysteine.

8. The YhhS variant according to claim 1, wherein isoleucine corresponding to 241st position in SEQ ID NO: 1 is substituted with threonine.

9. The YhhS variant according to claim 1, wherein valine corresponding to 330th position in SEQ ID NO: 1 is substituted with isoleucine.

10. A polynucleotide encoding the variant according to claim 2.

11. A polynucleotide encoding the variant according to claim 3.

12. A polynucleotide encoding the variant according to claim 8.

13. A YhhS variant, wherein serine corresponding to 129th position in SEQ ID NO: 1 is substituted with glycine.

14. A YhhS variant, wherein serine corresponding to 129th position in SEQ ID NO: 1 is substituted with alanine.

15. The YhhS variant according to claim 1, wherein the variant comprises SEQ ID NO: 2.

16. The YhhS variant according to claim 1, wherein the variant comprises SEQ ID NO: 3.

17. The YhhS variant according to claim 1, wherein the variant comprises SEQ ID NO: 34.

18. The YhhS variant according to claim 1, wherein the variant comprises SEQ ID NO: 36.

19. The YhhS variant according to claim 1, wherein isoleucine corresponding to 241st position in SEQ ID NO: 1 is substituted with glutamine or threonine, aspartic acid corresponding to 246th position in SEQ ID NO: 1 is substituted with valine, and valine corresponding to 330th position in SEQ ID NO: 1 is substituted with isoleucine.

* * * * *

SEQUENCE LISTING

```
<160> NUMBER OF SEQ ID NOS: 38

<210> SEQ ID NO 1
<211> LENGTH: 405
<212> TYPE: PRT
<213> ORGANISM: Unknown
<220> FEATURE:
<223> OTHER INFORMATION: YhhS(WT)

<400> SEQUENCE: 1

Met Pro Glu Pro Val Ala Glu Pro Ala Leu Asn Gly Leu Arg Leu Asn
1               5                   10                  15

Leu Arg Ile Val Ser Ile Val Met Phe Asn Phe Ala Ser Tyr Leu Thr
            20                  25                  30
```

```
Ile Gly Leu Pro Leu Ala Val Leu Pro Gly Tyr Val His Asp Val Met
        35                  40                  45

Gly Phe Ser Ala Phe Trp Ala Gly Leu Val Ile Ser Leu Gln Tyr Phe
    50                  55                  60

Ala Thr Leu Leu Ser Arg Pro His Ala Gly Arg Tyr Ala Asp Ser Leu
65                  70                  75                  80

Gly Pro Lys Lys Ile Val Val Phe Gly Leu Cys Gly Cys Phe Leu Ser
                85                  90                  95

Gly Leu Gly Tyr Leu Thr Ala Gly Leu Thr Ala Ser Leu Pro Val Ile
            100                 105                 110

Ser Leu Leu Leu Leu Cys Leu Gly Arg Val Ile Leu Gly Ile Gly Gln
        115                 120                 125

Ser Phe Ala Gly Thr Gly Ser Thr Leu Trp Gly Val Gly Val Val Gly
    130                 135                 140

Ser Leu His Ile Gly Arg Val Ile Ser Trp Asn Gly Ile Val Thr Tyr
145                 150                 155                 160

Gly Ala Met Ala Met Gly Ala Pro Leu Gly Val Val Phe Tyr His Trp
                165                 170                 175

Gly Gly Leu Gln Ala Leu Ala Leu Ile Ile Met Gly Val Ala Leu Val
            180                 185                 190

Ala Ile Leu Leu Ala Ile Pro Arg Pro Thr Val Lys Ala Ser Lys Gly
        195                 200                 205

Lys Pro Leu Pro Phe Arg Ala Val Leu Gly Arg Val Trp Leu Tyr Gly
    210                 215                 220

Met Ala Leu Ala Leu Ala Ser Ala Gly Phe Gly Val Ile Ala Thr Phe
225                 230                 235                 240

Ile Thr Leu Phe Tyr Asp Ala Lys Gly Trp Asp Gly Ala Ala Phe Ala
                245                 250                 255

Leu Thr Leu Phe Ser Cys Ala Phe Val Gly Thr Arg Leu Leu Phe Pro
            260                 265                 270

Asn Gly Ile Asn Arg Ile Gly Gly Leu Asn Val Ala Met Ile Cys Phe
        275                 280                 285

Ser Val Glu Ile Ile Gly Leu Leu Leu Val Gly Val Ala Thr Met Pro
    290                 295                 300

Trp Met Ala Lys Ile Gly Val Leu Leu Ala Gly Ala Gly Phe Ser Leu
305                 310                 315                 320

Val Phe Pro Ala Leu Gly Val Val Ala Val Lys Ala Val Pro Gln Gln
                325                 330                 335

Asn Gln Gly Ala Ala Leu Ala Thr Tyr Thr Val Phe Met Asp Leu Ser
            340                 345                 350

Leu Gly Val Thr Gly Pro Leu Ala Gly Leu Val Met Ser Trp Ala Gly
        355                 360                 365

Val Pro Val Ile Tyr Leu Ala Ala Ala Gly Leu Val Ala Ile Ala Leu
    370                 375                 380

Leu Leu Thr Trp Arg Leu Lys Lys Arg Pro Pro Glu His Val Pro Glu
385                 390                 395                 400

Ala Ala Ser Ser Ser
                405
```

<210> SEQ ID NO 2
<211> LENGTH: 405
<212> TYPE: PRT
<213> ORGANISM: Artificial Sequence
<220> FEATURE:
<223> OTHER INFORMATION: YhhS(S129G) AA

<400> SEQUENCE: 2

```
Met Pro Glu Pro Val Ala Glu Pro Ala Leu Asn Gly Leu Arg Leu Asn
1               5                   10                  15

Leu Arg Ile Val Ser Ile Val Met Phe Asn Phe Ala Ser Tyr Leu Thr
            20                  25                  30

Ile Gly Leu Pro Leu Ala Val Leu Pro Gly Tyr Val His Asp Val Met
        35                  40                  45

Gly Phe Ser Ala Phe Trp Ala Gly Leu Val Ile Ser Leu Gln Tyr Phe
    50                  55                  60

Ala Thr Leu Leu Ser Arg Pro His Ala Gly Arg Tyr Ala Asp Ser Leu
65                  70                  75                  80

Gly Pro Lys Lys Ile Val Val Phe Gly Leu Cys Gly Cys Phe Leu Ser
                85                  90                  95

Gly Leu Gly Tyr Leu Thr Ala Gly Leu Thr Ala Ser Leu Pro Val Ile
            100                 105                 110

Ser Leu Leu Leu Leu Cys Leu Gly Arg Val Ile Leu Gly Ile Gly Gln
        115                 120                 125

Gly Phe Ala Gly Thr Gly Ser Thr Leu Trp Gly Val Gly Val Val Gly
    130                 135                 140

Ser Leu His Ile Gly Arg Val Ile Ser Trp Asn Gly Ile Val Thr Tyr
145                 150                 155                 160

Gly Ala Met Ala Met Gly Ala Pro Leu Gly Val Val Phe Tyr His Trp
                165                 170                 175

Gly Gly Leu Gln Ala Leu Ala Leu Ile Ile Met Gly Val Ala Leu Val
            180                 185                 190

Ala Ile Leu Leu Ala Ile Pro Arg Pro Thr Val Lys Ala Ser Lys Gly
        195                 200                 205

Lys Pro Leu Pro Phe Arg Ala Val Leu Gly Arg Val Trp Leu Tyr Gly
    210                 215                 220

Met Ala Leu Ala Leu Ala Ser Ala Gly Phe Gly Val Ile Ala Thr Phe
225                 230                 235                 240

Ile Thr Leu Phe Tyr Asp Ala Lys Gly Trp Asp Gly Ala Ala Phe Ala
                245                 250                 255

Leu Thr Leu Phe Ser Cys Ala Phe Val Gly Thr Arg Leu Leu Phe Pro
            260                 265                 270

Asn Gly Ile Asn Arg Ile Gly Gly Leu Asn Val Ala Met Ile Cys Phe
        275                 280                 285

Ser Val Glu Ile Ile Gly Leu Leu Leu Val Gly Val Ala Thr Met Pro
    290                 295                 300

Trp Met Ala Lys Ile Gly Val Leu Leu Ala Gly Ala Gly Phe Ser Leu
305                 310                 315                 320

Val Phe Pro Ala Leu Gly Val Val Ala Val Lys Ala Val Pro Gln Gln
                325                 330                 335

Asn Gln Gly Ala Ala Leu Ala Thr Tyr Thr Val Phe Met Asp Leu Ser
            340                 345                 350

Leu Gly Val Thr Gly Pro Leu Ala Gly Leu Val Met Ser Trp Ala Gly
        355                 360                 365

Val Pro Val Ile Tyr Leu Ala Ala Ala Gly Leu Val Ala Ile Ala Leu
    370                 375                 380

Leu Leu Thr Trp Arg Leu Lys Lys Arg Pro Pro Glu His Val Pro Glu
385                 390                 395                 400

Ala Ala Ser Ser Ser
```

405

<210> SEQ ID NO 3
<211> LENGTH: 405
<212> TYPE: PRT
<213> ORGANISM: Artificial Sequence
<220> FEATURE:
<223> OTHER INFORMATION: YhhS(S129A) AA

<400> SEQUENCE: 3

Met Pro Glu Pro Val Ala Glu Pro Ala Leu Asn Gly Leu Arg Leu Asn
1 5 10 15

Leu Arg Ile Val Ser Ile Val Met Phe Asn Phe Ala Ser Tyr Leu Thr
20 25 30

Ile Gly Leu Pro Leu Ala Val Leu Pro Gly Tyr Val His Asp Val Met
35 40 45

Gly Phe Ser Ala Phe Trp Ala Gly Leu Val Ile Ser Leu Gln Tyr Phe
50 55 60

Ala Thr Leu Leu Ser Arg Pro His Ala Gly Arg Tyr Ala Asp Ser Leu
65 70 75 80

Gly Pro Lys Lys Ile Val Val Phe Gly Leu Cys Gly Cys Phe Leu Ser
85 90 95

Gly Leu Gly Tyr Leu Thr Ala Gly Leu Thr Ala Ser Leu Pro Val Ile
100 105 110

Ser Leu Leu Leu Leu Cys Leu Gly Arg Val Ile Leu Gly Ile Gly Gln
115 120 125

Ala Phe Ala Gly Thr Gly Ser Thr Leu Trp Gly Val Gly Val Val Gly
130 135 140

Ser Leu His Ile Gly Arg Val Ile Ser Trp Asn Gly Ile Val Thr Tyr
145 150 155 160

Gly Ala Met Ala Met Gly Ala Pro Leu Gly Val Val Phe Tyr His Trp
165 170 175

Gly Gly Leu Gln Ala Leu Ala Leu Ile Ile Met Gly Val Ala Leu Val
180 185 190

Ala Ile Leu Leu Ala Ile Pro Arg Pro Thr Val Lys Ala Ser Lys Gly
195 200 205

Lys Pro Leu Pro Phe Arg Ala Val Leu Gly Arg Val Trp Leu Tyr Gly
210 215 220

Met Ala Leu Ala Leu Ala Ser Ala Gly Phe Gly Val Ile Ala Thr Phe
225 230 235 240

Ile Thr Leu Phe Tyr Asp Ala Lys Gly Trp Asp Gly Ala Ala Phe Ala
245 250 255

Leu Thr Leu Phe Ser Cys Ala Phe Val Gly Thr Arg Leu Leu Phe Pro
260 265 270

Asn Gly Ile Asn Arg Ile Gly Gly Leu Asn Val Ala Met Ile Cys Phe
275 280 285

Ser Val Glu Ile Ile Gly Leu Leu Leu Val Gly Val Ala Thr Met Pro
290 295 300

Trp Met Ala Lys Ile Gly Val Leu Leu Ala Gly Ala Gly Phe Ser Leu
305 310 315 320

Val Phe Pro Ala Leu Gly Val Val Ala Val Lys Ala Val Pro Gln Gln
325 330 335

Asn Gln Gly Ala Ala Leu Ala Thr Tyr Thr Val Phe Met Asp Leu Ser
340 345 350

Leu Gly Val Thr Gly Pro Leu Ala Gly Leu Val Met Ser Trp Ala Gly

```
        355                 360                 365

Val Pro Val Ile Tyr Leu Ala Ala Ala Gly Leu Val Ala Ile Ala Leu
    370                 375                 380

Leu Leu Thr Trp Arg Leu Lys Lys Arg Pro Pro Glu His Val Pro Glu
385                 390                 395                 400

Ala Ala Ser Ser Ser
                405


<210> SEQ ID NO 4
<211> LENGTH: 405
<212> TYPE: PRT
<213> ORGANISM: Artificial Sequence
<220> FEATURE:
<223> OTHER INFORMATION: YhhS(I241Q) AA

<400> SEQUENCE: 4

Met Pro Glu Pro Val Ala Glu Pro Ala Leu Asn Gly Leu Arg Leu Asn
1               5                   10                  15

Leu Arg Ile Val Ser Ile Val Met Phe Asn Phe Ala Ser Tyr Leu Thr
            20                  25                  30

Ile Gly Leu Pro Leu Ala Val Leu Pro Gly Tyr Val His Asp Val Met
        35                  40                  45

Gly Phe Ser Ala Phe Trp Ala Gly Leu Val Ile Ser Leu Gln Tyr Phe
    50                  55                  60

Ala Thr Leu Leu Ser Arg Pro His Ala Gly Arg Tyr Ala Asp Ser Leu
65                  70                  75                  80

Gly Pro Lys Lys Ile Val Val Phe Gly Leu Cys Gly Cys Phe Leu Ser
                85                  90                  95

Gly Leu Gly Tyr Leu Thr Ala Gly Leu Thr Ala Ser Leu Pro Val Ile
            100                 105                 110

Ser Leu Leu Leu Leu Cys Leu Gly Arg Val Ile Leu Gly Ile Gly Gln
        115                 120                 125

Ser Phe Ala Gly Thr Gly Ser Thr Leu Trp Gly Val Gly Val Val Gly
    130                 135                 140

Ser Leu His Ile Gly Arg Val Ile Ser Trp Asn Gly Ile Val Thr Tyr
145                 150                 155                 160

Gly Ala Met Ala Met Gly Ala Pro Leu Gly Val Val Phe Tyr His Trp
                165                 170                 175

Gly Gly Leu Gln Ala Leu Ala Leu Ile Ile Met Gly Val Ala Leu Val
            180                 185                 190

Ala Ile Leu Leu Ala Ile Pro Arg Pro Thr Val Lys Ala Ser Lys Gly
        195                 200                 205

Lys Pro Leu Pro Phe Arg Ala Val Leu Gly Arg Val Trp Leu Tyr Gly
    210                 215                 220

Met Ala Leu Ala Leu Ala Ser Ala Gly Phe Gly Val Ile Ala Thr Phe
225                 230                 235                 240

Gln Thr Leu Phe Tyr Asp Ala Lys Gly Trp Asp Gly Ala Ala Phe Ala
                245                 250                 255

Leu Thr Leu Phe Ser Cys Ala Phe Val Gly Thr Arg Leu Leu Phe Pro
            260                 265                 270

Asn Gly Ile Asn Arg Ile Gly Gly Leu Asn Val Ala Met Ile Cys Phe
        275                 280                 285

Ser Val Glu Ile Ile Gly Leu Leu Leu Val Gly Val Ala Thr Met Pro
    290                 295                 300

Trp Met Ala Lys Ile Gly Val Leu Leu Ala Gly Ala Gly Phe Ser Leu
```

```
305                 310                 315                 320

Val Phe Pro Ala Leu Gly Val Val Ala Val Lys Ala Val Pro Gln Gln
                325                 330                 335

Asn Gln Gly Ala Ala Leu Ala Thr Tyr Thr Val Phe Met Asp Leu Ser
            340                 345                 350

Leu Gly Val Thr Gly Pro Leu Ala Gly Leu Val Met Ser Trp Ala Gly
        355                 360                 365

Val Pro Val Ile Tyr Leu Ala Ala Ala Gly Leu Val Ala Ile Ala Leu
    370                 375                 380

Leu Leu Thr Trp Arg Leu Lys Lys Arg Pro Pro Glu His Val Pro Glu
385                 390                 395                 400

Ala Ala Ser Ser Ser
                405


<210> SEQ ID NO 5
<211> LENGTH: 405
<212> TYPE: PRT
<213> ORGANISM: Artificial Sequence
<220> FEATURE:
<223> OTHER INFORMATION: YhhS(I241T) AA

<400> SEQUENCE: 5

Met Pro Glu Pro Val Ala Glu Pro Ala Leu Asn Gly Leu Arg Leu Asn
1               5                   10                  15

Leu Arg Ile Val Ser Ile Val Met Phe Asn Phe Ala Ser Tyr Leu Thr
            20                  25                  30

Ile Gly Leu Pro Leu Ala Val Leu Pro Gly Tyr Val His Asp Val Met
        35                  40                  45

Gly Phe Ser Ala Phe Trp Ala Gly Leu Val Ile Ser Leu Gln Tyr Phe
    50                  55                  60

Ala Thr Leu Leu Ser Arg Pro His Ala Gly Arg Tyr Ala Asp Ser Leu
65                  70                  75                  80

Gly Pro Lys Lys Ile Val Val Phe Gly Leu Cys Gly Cys Phe Leu Ser
                85                  90                  95

Gly Leu Gly Tyr Leu Thr Ala Gly Leu Thr Ala Ser Leu Pro Val Ile
            100                 105                 110

Ser Leu Leu Leu Leu Cys Leu Gly Arg Val Ile Leu Gly Ile Gly Gln
        115                 120                 125

Ser Phe Ala Gly Thr Gly Ser Thr Leu Trp Gly Val Gly Val Val Gly
    130                 135                 140

Ser Leu His Ile Gly Arg Val Ile Ser Trp Asn Gly Ile Val Thr Tyr
145                 150                 155                 160

Gly Ala Met Ala Met Gly Ala Pro Leu Gly Val Val Phe Tyr His Trp
                165                 170                 175

Gly Gly Leu Gln Ala Leu Ala Leu Ile Ile Met Gly Val Ala Leu Val
            180                 185                 190

Ala Ile Leu Leu Ala Ile Pro Arg Pro Thr Val Lys Ala Ser Lys Gly
        195                 200                 205

Lys Pro Leu Pro Phe Arg Ala Val Leu Gly Arg Val Trp Leu Tyr Gly
    210                 215                 220

Met Ala Leu Ala Leu Ala Ser Ala Gly Phe Gly Val Ile Ala Thr Phe
225                 230                 235                 240

Thr Thr Leu Phe Tyr Asp Ala Lys Gly Trp Asp Gly Ala Ala Phe Ala
                245                 250                 255

Leu Thr Leu Phe Ser Cys Ala Phe Val Gly Thr Arg Leu Leu Phe Pro
```

```
            260                 265                 270

Asn Gly Ile Asn Arg Ile Gly Gly Leu Asn Val Ala Met Ile Cys Phe
        275                 280                 285

Ser Val Glu Ile Ile Gly Leu Leu Leu Val Gly Val Ala Thr Met Pro
    290                 295                 300

Trp Met Ala Lys Ile Gly Val Leu Leu Ala Gly Ala Gly Phe Ser Leu
305                 310                 315                 320

Val Phe Pro Ala Leu Gly Val Val Ala Val Lys Ala Val Pro Gln Gln
                325                 330                 335

Asn Gln Gly Ala Ala Leu Ala Thr Tyr Thr Val Phe Met Asp Leu Ser
            340                 345                 350

Leu Gly Val Thr Gly Pro Leu Ala Gly Leu Val Met Ser Trp Ala Gly
        355                 360                 365

Val Pro Val Ile Tyr Leu Ala Ala Ala Gly Leu Val Ala Ile Ala Leu
    370                 375                 380

Leu Leu Thr Trp Arg Leu Lys Lys Arg Pro Pro Glu His Val Pro Glu
385                 390                 395                 400

Ala Ala Ser Ser Ser
                405
```

<210> SEQ ID NO 6
<211> LENGTH: 1218
<212> TYPE: DNA
<213> ORGANISM: Artificial Sequence
<220> FEATURE:
<223> OTHER INFORMATION: YhhS(S129G) NT

<400> SEQUENCE: 6

```
atgcccgaac ccgtagccga acccgcgcta aacggattgc gcctgaattt gcgcattgtc     60

tctatagtca tgtttaactt cgccagctac ctcaccatcg ggttgccgct cgctgtatta    120

ccgggctatg tccatgatgt gatgggcttt agcgccttct gggcaggatt ggttatcagc    180

ctgcaatatt tcgccacctt gctgagccgc cctcatgccg gacgttacgc cgattcgctg    240

ggacccaaaa agattgtcgt cttcggttta tgcggctgct ttttgagcgg tctggggtat    300

ctgacggcag gattaaccgc cagtctgcct gtcatcagcc tgttattact ttgcctgggg    360

cgcgtcatcc ttgggattgg gcaaggtttt gccggaacgg gatcgaccct atggggcgtt    420

ggcgtggttg gctcgctgca tatcgggcgg gtgatttcgt ggaacggcat tgtcacttac    480

ggggcgatgg cgatgggtgc gccgttaggc gtcgtgtttt atcactgggg cggcttgcag    540

gcgttagcgt taatcattat gggcgtggcg ctggtggcca ttttgttggc gatcccgcgt    600

ccgacggtaa aagccagtaa aggcaaaccg ctgccgtttc gcgcggtgct tgggcgcgtc    660

tggctgtacg gtatggcgct ggcactggct tccgccggat ttggcgtcat cgccaccttt    720

atcacgctgt tttatgacgc taaaggttgg gacggtgcgg ctttcgcgct gacgctgttt    780

agctgtgcgt ttgtcggtac gcgtttgtta ttccctaacg gcattaaccg tatcggtggc    840

ttaaacgtag cgatgatttg ctttagcgtt gagataatcg gcctgctact ggttggcgtg    900

gcgactatgc cgtggatggc gaaaatcggc gtcttactgg cgggggccgg gttttcgctg    960

gtgttcccgg cattgggtgt agtggcggta aaagcggttc cgcagcaaaa tcagggggcg   1020

gcgctggcaa cttacaccgt atttatggat ttatcgcttg gcgtgactgg accactggct   1080

gggctggtga tgagctgggc gggcgtaccg gtgatttatc tggcggcggc gggactggtc   1140

gcaatcgcgt tattactgac gtggcgatta aaaaaacggc ctccggaaca cgtccctgag   1200
```

gccgcctcat catcttaa 1218

<210> SEQ ID NO 7
<211> LENGTH: 1218
<212> TYPE: DNA
<213> ORGANISM: Artificial Sequence
<220> FEATURE:
<223> OTHER INFORMATION: YhhS(S129A) NT

<400> SEQUENCE: 7
atgcccgaac ccgtagccga acccgcgcta aacggattgc gcctgaattt gcgcattgtc 60
tctatagtca tgtttaactt cgccagctac ctcaccatcg ggttgccgct cgctgtatta 120
ccgggctatg tccatgatgt gatgggcttt agcgccttct gggcaggatt ggttatcagc 180
ctgcaatatt tcgccacctt gctgagccgc cctcatgccg gacgttacgc cgattcgctg 240
ggacccaaaa agattgtcgt cttcggttta tgcggctgct ttttgagcgg tctggggtat 300
ctgacggcag gattaaccgc cagtctgcct gtcatcagcc tgttattact ttgcctgggg 360
cgcgtcatcc ttgggattgg gcaagcgttt gccggaacgg gatcgaccct atggggcgtt 420
ggcgtggttg gctcgctgca tatcgggcgg gtgatttcgt ggaacggcat tgtcacttac 480
ggggcgatgg cgatgggtgc gccgttaggc gtcgtgtttt atcactgggg cggcttgcag 540
gcgttagcgt taatcattat gggcgtggcg ctggtggcca ttttgttggc gatcccgcgt 600
ccgacggtaa aagccagtaa aggcaaaccg ctgccgtttc gcgcggtgct tgggcgcgtc 660
tggctgtacg gtatggcgct ggcactggct tccgccggat ttggcgtcat cgccaccttt 720
atcacgctgt tttatgacgc taaaggttgg gacggtgcgg ctttcgcgct gacgctgttt 780
agctgtgcgt ttgtcggtac gcgtttgtta ttccctaacg gcattaaccg tatcggtggc 840
ttaaacgtag cgatgatttg ctttagcgtt gagataatcg gcctgctact ggttggcgtg 900
gcgactatgc cgtggatggc gaaaatcggc gtcttactgg cgggggccgg gttttcgctg 960
gtgttcccgg cattgggtgt agtggcggta aaagcggttc cgcagcaaaa tcagggggcg 1020
gcgctggcaa cttacaccgt atttatggat ttatcgcttg gcgtgactgg accactggct 1080
gggctggtga tgagctgggc gggcgtaccg gtgatttatc tggcggcggc gggactggtc 1140
gcaatcgcgt tattactgac gtggcgatta aaaaaacggc ctccggaaca cgtccctgag 1200
gccgcctcat catcttaa 1218

<210> SEQ ID NO 8
<211> LENGTH: 1218
<212> TYPE: DNA
<213> ORGANISM: Artificial Sequence
<220> FEATURE:
<223> OTHER INFORMATION: YhhS(I241Q) NT

<400> SEQUENCE: 8
atgcccgaac ccgtagccga acccgcgcta aacggattgc gcctgaattt gcgcattgtc 60
tctatagtca tgtttaactt cgccagctac ctcaccatcg ggttgccgct cgctgtatta 120
ccgggctatg tccatgatgt gatgggcttt agcgccttct gggcaggatt ggttatcagc 180
ctgcaatatt tcgccacctt gctgagccgc cctcatgccg gacgttacgc cgattcgctg 240
ggacccaaaa agattgtcgt cttcggttta tgcggctgct ttttgagcgg tctggggtat 300
ctgacggcag gattaaccgc cagtctgcct gtcatcagcc tgttattact ttgcctgggg 360
cgcgtcatcc ttgggattgg gcaaagtttt gccggaacgg gatcgaccct atggggcgtt 420
ggcgtggttg gctcgctgca tatcgggcgg gtgatttcgt ggaacggcat tgtcacttac 480

```
ggggcgatgg cgatgggtgc gccgttaggc gtcgtgtttt atcactgggg cggcttgcag    540

gcgttagcgt taatcattat gggcgtggcg ctggtggcca ttttgttggc gatcccgcgt    600

ccgacggtaa aagccagtaa aggcaaaccg ctgccgtttc gcgcggtgct tgggcgcgtc    660

tggctgtacg gtatggcgct ggcactggct tccgccggat ttggcgtcat cgccaccttt    720

cagacgctgt tttatgacgc taaaggttgg gacggtgcgg ctttcgcgct gacgctgttt    780

agctgtgcgt ttgtcggtac gcgtttgtta ttccctaacg gcattaaccg tatcggtggc    840

ttaaacgtag cgatgatttg ctttagcgtt gagataatcg gcctgctact ggttggcgtg    900

gcgactatgc cgtggatggc gaaaatcggc gtcttactgg cgggggccgg gttttcgctg    960

gtgttcccgg cattgggtgt agtggcggta aaagcggttc cgcagcaaaa tcagggggcg   1020

gcgctggcaa cttacaccgt atttatggat ttatcgcttg gcgtgactgg accactggct   1080

gggctggtga tgagctgggc gggcgtaccg gtgatttatc tggcggcggc gggactggtc   1140

gcaatcgcgt tattactgac gtggcgatta aaaaaacggc ctccggaaca cgtccctgag   1200

gccgcctcat catcttaa                                                 1218
```

<210> SEQ ID NO 9
<211> LENGTH: 1218
<212> TYPE: DNA
<213> ORGANISM: Artificial Sequence
<220> FEATURE:
<223> OTHER INFORMATION: YhhS(I241T) NT

<400> SEQUENCE: 9

```
atgcccgaac ccgtagccga acccgcgcta aacggattgc gcctgaattt gcgcattgtc     60

tctatagtca tgtttaactt cgccagctac ctcaccatcg ggttgccgct cgctgtatta    120

ccgggctatg tccatgatgt gatgggcttt agcgccttct gggcaggatt ggttatcagc    180

ctgcaatatt tcgccacctt gctgagccgc cctcatgccg gacgttacgc cgattcgctg    240

ggacccaaaa agattgtcgt cttcggttta tgcggctgct tttgagcggg tctggggtat    300

ctgacggcag gattaaccgc cagtctgcct gtcatcagcc tgttattact ttgcctgggg    360

cgcgtcatcc ttgggattgg gcaaagtttt gccggaacgg gatcgaccct atggggcgtt    420

ggcgtggttg gctcgctgca tatcgggcgg gtgatttcgt ggaacggcat tgtcacttac    480

ggggcgatgg cgatgggtgc gccgttaggc gtcgtgtttt atcactgggg cggcttgcag    540

gcgttagcgt taatcattat gggcgtggcg ctggtggcca ttttgttggc gatcccgcgt    600

ccgacggtaa aagccagtaa aggcaaaccg ctgccgtttc gcgcggtgct tgggcgcgtc    660

tggctgtacg gtatggcgct ggcactggct tccgccggat ttggcgtcat cgccaccttt    720

accacgctgt tttatgacgc taaaggttgg gacggtgcgg ctttcgcgct gacgctgttt    780

agctgtgcgt ttgtcggtac gcgtttgtta ttccctaacg gcattaaccg tatcggtggc    840

ttaaacgtag cgatgatttg ctttagcgtt gagataatcg gcctgctact ggttggcgtg    900

gcgactatgc cgtggatggc gaaaatcggc gtcttactgg cgggggccgg gttttcgctg    960

gtgttcccgg cattgggtgt agtggcggta aaagcggttc cgcagcaaaa tcagggggcg   1020

gcgctggcaa cttacaccgt atttatggat ttatcgcttg gcgtgactgg accactggct   1080

gggctggtga tgagctgggc gggcgtaccg gtgatttatc tggcggcggc gggactggtc   1140

gcaatcgcgt tattactgac gtggcgatta aaaaaacggc ctccggaaca cgtccctgag   1200

gccgcctcat catcttaa                                                 1218
```

<210> SEQ ID NO 10
<211> LENGTH: 322
<212> TYPE: PRT
<213> ORGANISM: Unknown
<220> FEATURE:
<223> OTHER INFORMATION: SerB

<400> SEQUENCE: 10

```
Met Pro Asn Ile Thr Trp Cys Asp Leu Pro Glu Asp Val Ser Leu Trp
1               5                   10                  15

Pro Gly Leu Pro Leu Ser Leu Ser Gly Asp Glu Val Met Pro Leu Asp
            20                  25                  30

Tyr His Ala Gly Arg Ser Gly Trp Leu Leu Tyr Gly Arg Gly Leu Asp
        35                  40                  45

Lys Gln Arg Leu Thr Gln Tyr Gln Ser Lys Leu Gly Ala Ala Met Val
    50                  55                  60

Ile Val Ala Ala Trp Cys Val Glu Asp Tyr Gln Val Ile Arg Leu Ala
65                  70                  75                  80

Gly Ser Leu Thr Ala Arg Ala Thr Arg Leu Ala His Glu Ala Gln Leu
                85                  90                  95

Asp Val Ala Pro Leu Gly Lys Ile Pro His Leu Arg Thr Pro Gly Leu
            100                 105                 110

Leu Val Met Asp Met Asp Ser Thr Ala Ile Gln Ile Glu Cys Ile Asp
        115                 120                 125

Glu Ile Ala Lys Leu Ala Gly Thr Gly Glu Met Val Ala Glu Val Thr
    130                 135                 140

Glu Arg Ala Met Arg Gly Glu Leu Asp Phe Thr Ala Ser Leu Arg Ser
145                 150                 155                 160

Arg Val Ala Thr Leu Lys Gly Ala Asp Ala Asn Ile Leu Gln Gln Val
                165                 170                 175

Arg Glu Asn Leu Pro Leu Met Pro Gly Leu Thr Gln Leu Val Leu Lys
            180                 185                 190

Leu Glu Thr Leu Gly Trp Lys Val Ala Ile Ala Ser Gly Gly Phe Thr
        195                 200                 205

Phe Phe Ala Glu Tyr Leu Arg Asp Lys Leu Arg Leu Thr Ala Val Val
    210                 215                 220

Ala Asn Glu Leu Glu Ile Met Asp Gly Lys Phe Thr Gly Asn Val Ile
225                 230                 235                 240

Gly Asp Ile Val Asp Ala Gln Tyr Lys Ala Lys Thr Leu Thr Arg Leu
                245                 250                 255

Ala Gln Glu Tyr Glu Ile Pro Leu Ala Gln Thr Val Ala Ile Gly Asp
            260                 265                 270

Gly Ala Asn Asp Leu Pro Met Ile Lys Ala Ala Gly Leu Gly Ile Ala
        275                 280                 285

Tyr His Ala Lys Pro Lys Val Asn Glu Lys Ala Glu Val Thr Ile Arg
    290                 295                 300

His Ala Asp Leu Met Gly Val Phe Cys Ile Leu Ser Gly Ser Leu Asn
305                 310                 315                 320

Gln Lys
```

<210> SEQ ID NO 11
<211> LENGTH: 969
<212> TYPE: DNA
<213> ORGANISM: Unknown
<220> FEATURE:
<223> OTHER INFORMATION: SerB

<400> SEQUENCE: 11

```
atgcctaaca ttacctggtg cgacctgcct gaagatgtct ctttatggcc gggtctgcct      60

ctttcattaa gtggtgatga agtgatgcca ctggattacc acgcaggtcg tagcggctgg     120

ctgctgtatg gtcgtgggct ggataaacaa cgtctgaccc aataccagag caaactgggt     180

gcggcgatgg tgattgttgc cgcctggtgc gtggaagatt atcaggtgat tcgtctggca     240

ggttcactca ccgcacgggc tacacgcctg gcccacgaag cgcagctgga tgtcgccccg     300

ctggggaaaa tcccgcacct gcgcacgccg ggtttgctgg tgatggatat ggactccacc     360

gccatccaga ttgaatgtat tgatgaaatt gccaaactgg ccggaacggg cgagatggtg     420

gcggaagtaa ccgaacgggc gatgcgcggc gaactcgatt ttaccgccag cctgcgcagc     480

cgtgtggcga cgctgaaagg cgctgacgcc aatattctgc aacaggtgcg tgaaaatctg     540

ccgctgatgc caggcttaac gcaactggtg ctcaagctgg aaacgctggg ctggaaagtg     600

gcgattgcct ccggcggctt tactttcttt gctgaatacc tgcgcgacaa gctgcgcctg     660

accgccgtgg tagccaatga actggagatc atggacggta aatttaccgg caatgtgatc     720

ggcgacatcg tagacgcgca gtacaaagcg aaaactctga ctcgcctcgc gcaggagtat     780

gaaatcccgc tggcgcagac cgtggcgatt ggcgatggag ccaatgacct gccgatgatc     840

aaagcggcag ggctggggat tgcctaccat gccaagccaa aagtgaatga aaaggcggaa     900

gtcaccatcc gtcacgctga cctgatgggg gtattctgca tcctctcagg cagcctgaat     960

cagaagtaa                                                             969
```

<210> SEQ ID NO 12
<211> LENGTH: 405
<212> TYPE: PRT
<213> ORGANISM: Artificial Sequence
<220> FEATURE:
<223> OTHER INFORMATION: YhhS(I241T/D246V/V330I) AA

<400> SEQUENCE: 12

```
Met Pro Glu Pro Val Ala Glu Pro Ala Leu Asn Gly Leu Arg Leu Asn
1               5                   10                  15

Leu Arg Ile Val Ser Ile Val Met Phe Asn Phe Ala Ser Tyr Leu Thr
            20                  25                  30

Ile Gly Leu Pro Leu Ala Val Leu Pro Gly Tyr Val His Asp Val Met
        35                  40                  45

Gly Phe Ser Ala Phe Trp Ala Gly Leu Val Ile Ser Leu Gln Tyr Phe
    50                  55                  60

Ala Thr Leu Leu Ser Arg Pro His Ala Gly Arg Tyr Ala Asp Ser Leu
65                  70                  75                  80

Gly Pro Lys Lys Ile Val Val Phe Gly Leu Cys Gly Cys Phe Leu Ser
                85                  90                  95

Gly Leu Gly Tyr Leu Thr Ala Gly Leu Thr Ala Ser Leu Pro Val Ile
            100                 105                 110

Ser Leu Leu Leu Leu Cys Leu Gly Arg Val Ile Leu Gly Ile Gly Gln
        115                 120                 125

Ser Phe Ala Gly Thr Gly Ser Thr Leu Trp Gly Val Gly Val Val Gly
    130                 135                 140

Ser Leu His Ile Gly Arg Val Ile Ser Trp Asn Gly Ile Val Thr Tyr
145                 150                 155                 160

Gly Ala Met Ala Met Gly Ala Pro Leu Gly Val Val Phe Tyr His Trp
                165                 170                 175
```

```
Gly Gly Leu Gln Ala Leu Ala Leu Ile Ile Met Gly Val Ala Leu Val
            180                 185                 190

Ala Ile Leu Leu Ala Ile Pro Arg Pro Thr Val Lys Ala Ser Lys Gly
        195                 200                 205

Lys Pro Leu Pro Phe Arg Ala Val Leu Gly Arg Val Trp Leu Tyr Gly
    210                 215                 220

Met Ala Leu Ala Leu Ala Ser Ala Gly Phe Gly Val Ile Ala Thr Phe
225                 230                 235                 240

Thr Thr Leu Phe Tyr Val Ala Lys Gly Trp Asp Gly Ala Ala Phe Ala
                245                 250                 255

Leu Thr Leu Phe Ser Cys Ala Phe Val Gly Thr Arg Leu Leu Phe Pro
            260                 265                 270

Asn Gly Ile Asn Arg Ile Gly Gly Leu Asn Val Ala Met Ile Cys Phe
        275                 280                 285

Ser Val Glu Ile Ile Gly Leu Leu Leu Val Gly Val Ala Thr Met Pro
    290                 295                 300

Trp Met Ala Lys Ile Gly Val Leu Leu Ala Gly Ala Gly Phe Ser Leu
305                 310                 315                 320

Val Phe Pro Ala Leu Gly Val Val Ala Ile Lys Ala Val Pro Gln Gln
                325                 330                 335

Asn Gln Gly Ala Ala Leu Ala Thr Tyr Thr Val Phe Met Asp Leu Ser
            340                 345                 350

Leu Gly Val Thr Gly Pro Leu Ala Gly Leu Val Met Ser Trp Ala Gly
        355                 360                 365

Val Pro Val Ile Tyr Leu Ala Ala Ala Gly Leu Val Ala Ile Ala Leu
    370                 375                 380

Leu Leu Thr Trp Arg Leu Lys Lys Arg Pro Pro Glu His Val Pro Glu
385                 390                 395                 400

Ala Ala Ser Ser Ser
                405


<210> SEQ ID NO 13
<211> LENGTH: 31
<212> TYPE: DNA
<213> ORGANISM: Artificial Sequence
<220> FEATURE:
<223> OTHER INFORMATION: K12_F

<400> SEQUENCE: 13

ggagttcatc agtatgcccg aacccgtagc c                                 31


<210> SEQ ID NO 14
<211> LENGTH: 32
<212> TYPE: DNA
<213> ORGANISM: Artificial Sequence
<220> FEATURE:
<223> OTHER INFORMATION: K12_R

<400> SEQUENCE: 14

ctgcaggtcg aagtttaaga tgatgaggcg gc                                32


<210> SEQ ID NO 15
<211> LENGTH: 39
<212> TYPE: DNA
<213> ORGANISM: Artificial Sequence
<220> FEATURE:
<223> OTHER INFORMATION: rhtB promoter_F

<400> SEQUENCE: 15
```

cgacggccag tgaattcgat ggtcgatgat taagacatc 39

<210> SEQ ID NO 16
<211> LENGTH: 41
<212> TYPE: DNA
<213> ORGANISM: Artificial Sequence
<220> FEATURE:
<223> OTHER INFORMATION: rhtB promoter_R

<400> SEQUENCE: 16
atgcctgcag gtcgaagtac tgatgaactc ccggtgtgtc t 41

<210> SEQ ID NO 17
<211> LENGTH: 1218
<212> TYPE: DNA
<213> ORGANISM: Artificial Sequence
<220> FEATURE:
<223> OTHER INFORMATION: YhhS(I241T/D246V/V330I) NT

<400> SEQUENCE: 17
atgcccgaac ccgtagccga acccgcgcta aacggattgc gcctgaattt gcgcattgtc 60
tctatagtca tgtttaactt cgccagctac ctcaccatcg ggttgccgct cgctgtatta 120
ccgggctatg tccatgatgt gatgggcttt agcgccttct gggcaggatt ggttatcagc 180
ctgcaatatt tcgccacctt gctgagccgc cctcatgccg gacgttacgc cgattcgctg 240
ggacccaaaa agattgtcgt cttcggttta tgcggctgct ttttgagcgg tctggggtat 300
ctgacggcag gattaaccgc cagtctgcct gtcatcagcc tgttattact ttgcctgggg 360
cgcgtcatcc ttgggattgg gcaaagtttt gccggaacgg gatcgaccct atggggcgtt 420
ggcgtggttg gctcgctgca tatcgggcgg gtgatttcgt ggaacggcat tgtcacttac 480
ggggcgatgg cgatgggtgc gccgttaggc gtcgtgtttt atcactgggg cggcttgcag 540
gcgttagcgt taatcattat gggcgtggcg ctggtggcca ttttgttggc gatcccgcgt 600
ccgacggtaa aagccagtaa aggcaaaccg ctgccgtttc gcgcggtgct tgggcgcgtc 660
tggctgtacg gtatggcgct ggcactggct tccgccggat ttggcgtcat cgccaccttt 720
accacgctgt tttatgtcgc taaaggttgg gacggtgcgg ctttcgcgct gacgctgttt 780
agctgtgcgt ttgtcggtac gcgtttgtta ttccctaacg gcattaaccg tatcggtggc 840
ttaaacgtag cgatgatttg ctttagcgtt gagataatcg gcctgctact ggttggcgtg 900
gcgactatgc cgtggatggc gaaaatcggc gtcttactgg cgggggccgg gttttcgctg 960
gtgttcccgg cattgggtgt agtggcgata aaagcggttc cgcagcaaaa tcagggggcg 1020
gcgctggcaa cttacaccgt atttatggat ttatcgcttg gcgtgactgg accactggct 1080
gggctggtga tgagctgggc gggcgtaccg gtgatttatc tggcggcggc gggactggtc 1140
gcaatcgcgt tattactgac gtggcgatta aaaaaacggc ctccggaaca cgtccctgag 1200
gccgcctcat catcttaa 1218

<210> SEQ ID NO 18
<211> LENGTH: 35
<212> TYPE: DNA
<213> ORGANISM: Artificial Sequence
<220> FEATURE:
<223> OTHER INFORMATION: YhhS(S129A) up_R

<400> SEQUENCE: 18
tcccgttccg gcaaacgctt gcccaatccc aagga 35

<210> SEQ ID NO 19
<211> LENGTH: 35
<212> TYPE: DNA
<213> ORGANISM: Artificial Sequence
<220> FEATURE:
<223> OTHER INFORMATION: YhhS(S129A) down_F

<400> SEQUENCE: 19
cttgggattg ggcaagcgtt tgccggaacg ggatc 35

<210> SEQ ID NO 20
<211> LENGTH: 35
<212> TYPE: DNA
<213> ORGANISM: Artificial Sequence
<220> FEATURE:
<223> OTHER INFORMATION: mgsA up_F

<400> SEQUENCE: 20
cctgccatcg gatccggtat ccgtttttgc cacca 35

<210> SEQ ID NO 21
<211> LENGTH: 35
<212> TYPE: DNA
<213> ORGANISM: Artificial Sequence
<220> FEATURE:
<223> OTHER INFORMATION: mgsA up_R

<400> SEQUENCE: 21
acctgtgcaa taagtactaa tgtacatccg tagtt 35

<210> SEQ ID NO 22
<211> LENGTH: 35
<212> TYPE: DNA
<213> ORGANISM: Artificial Sequence
<220> FEATURE:
<223> OTHER INFORMATION: mgsA down_F

<400> SEQUENCE: 22
cggatgtaca ttagtactta ttgcacaggt ggcaa 35

<210> SEQ ID NO 23
<211> LENGTH: 35
<212> TYPE: DNA
<213> ORGANISM: Artificial Sequence
<220> FEATURE:
<223> OTHER INFORMATION: mgsA down_R

<400> SEQUENCE: 23
tgatatcgaa ttccttcgct gttggtgatg actgg 35

<210> SEQ ID NO 24
<211> LENGTH: 35
<212> TYPE: DNA
<213> ORGANISM: Artificial Sequence
<220> FEATURE:
<223> OTHER INFORMATION: trc promoter_F

<400> SEQUENCE: 24
cggatgtaca ttagtcgctt gctgcaactc tctca 35

<210> SEQ ID NO 25
<211> LENGTH: 35
<212> TYPE: DNA
<213> ORGANISM: Artificial Sequence
<220> FEATURE:
<223> OTHER INFORMATION: trc promoter_R

<400> SEQUENCE: 25
gatagctctc ctgtgtgaaa ttgttatccg ctcac 35

<210> SEQ ID NO 26
<211> LENGTH: 35
<212> TYPE: DNA
<213> ORGANISM: Artificial Sequence
<220> FEATURE:
<223> OTHER INFORMATION: YhhS(I241T/D246V/V330I) ORF_F

<400> SEQUENCE: 26
cacaggaaag atatcatgcc cgaacccgta gccga 35

<210> SEQ ID NO 27
<211> LENGTH: 35
<212> TYPE: DNA
<213> ORGANISM: Artificial Sequence
<220> FEATURE:
<223> OTHER INFORMATION: YhhS(I241T/D246V/V330I) ORF_R

<400> SEQUENCE: 27
acctgtgcaa taagtttaag atgatgaggc ggcct 35

<210> SEQ ID NO 28
<211> LENGTH: 48
<212> TYPE: DNA
<213> ORGANISM: Artificial Sequence
<220> FEATURE:
<223> OTHER INFORMATION: I241Q up_F

<400> SEQUENCE: 28
gccggatttg gcgtcatcgc cacctttcag acgctgtttt atgacgct 48

<210> SEQ ID NO 29
<211> LENGTH: 48
<212> TYPE: DNA
<213> ORGANISM: Artificial Sequence
<220> FEATURE:
<223> OTHER INFORMATION: I241Q down_R

<400> SEQUENCE: 29
ccaaccttta gcgtcataaa acagcgtctg aaaggtggcg atgacgcc 48

<210> SEQ ID NO 30
<211> LENGTH: 35
<212> TYPE: DNA
<213> ORGANISM: Artificial Sequence
<220> FEATURE:
<223> OTHER INFORMATION: I241T up_R

<400> SEQUENCE: 30
tcataaaaca gcgtggtaaa ggtggcgatg acgcc 35

<210> SEQ ID NO 31
<211> LENGTH: 35
<212> TYPE: DNA
<213> ORGANISM: Artificial Sequence
<220> FEATURE:
<223> OTHER INFORMATION: I241T up_F

<400> SEQUENCE: 31
tcatcgccac ctttaccacg ctgttttatg acgct 35

<210> SEQ ID NO 32

<211> LENGTH: 20
<212> TYPE: DNA
<213> ORGANISM: Artificial Sequence
<220> FEATURE:
<223> OTHER INFORMATION: PCR_129G_F

<400> SEQUENCE: 32
attgggcaag gttttgccgg 20

<210> SEQ ID NO 33
<211> LENGTH: 20
<212> TYPE: DNA
<213> ORGANISM: Artificial Sequence
<220> FEATURE:
<223> OTHER INFORMATION: PCR_129G_R

<400> SEQUENCE: 33
ccggcaaaac cttgcccaat 20

<210> SEQ ID NO 34
<211> LENGTH: 405
<212> TYPE: PRT
<213> ORGANISM: Artificial Sequence
<220> FEATURE:
<223> OTHER INFORMATION: YhhS(S129G/I241T/D246V/V330I) AA

<400> SEQUENCE: 34

Met Pro Glu Pro Val Ala Glu Pro Ala Leu Asn Gly Leu Arg Leu Asn
1 5 10 15

Leu Arg Ile Val Ser Ile Val Met Phe Asn Phe Ala Ser Tyr Leu Thr
20 25 30

Ile Gly Leu Pro Leu Ala Val Leu Pro Gly Tyr Val His Asp Val Met
35 40 45

Gly Phe Ser Ala Phe Trp Ala Gly Leu Val Ile Ser Leu Gln Tyr Phe
50 55 60

Ala Thr Leu Leu Ser Arg Pro His Ala Gly Arg Tyr Ala Asp Ser Leu
65 70 75 80

Gly Pro Lys Lys Ile Val Val Phe Gly Leu Cys Gly Cys Phe Leu Ser
85 90 95

Gly Leu Gly Tyr Leu Thr Ala Gly Leu Thr Ala Ser Leu Pro Val Ile
100 105 110

Ser Leu Leu Leu Leu Cys Leu Gly Arg Val Ile Leu Gly Ile Gly Gln
115 120 125

Gly Phe Ala Gly Thr Gly Ser Thr Leu Trp Gly Val Gly Val Val Gly
130 135 140

Ser Leu His Ile Gly Arg Val Ile Ser Trp Asn Gly Ile Val Thr Tyr
145 150 155 160

Gly Ala Met Ala Met Gly Ala Pro Leu Gly Val Val Phe Tyr His Trp
165 170 175

Gly Gly Leu Gln Ala Leu Ala Leu Ile Ile Met Gly Val Ala Leu Val
180 185 190

Ala Ile Leu Leu Ala Ile Pro Arg Pro Thr Val Lys Ala Ser Lys Gly
195 200 205

Lys Pro Leu Pro Phe Arg Ala Val Leu Gly Arg Val Trp Leu Tyr Gly
210 215 220

Met Ala Leu Ala Leu Ala Ser Ala Gly Phe Gly Val Ile Ala Thr Phe
225 230 235 240

Thr Thr Leu Phe Tyr Val Ala Lys Gly Trp Asp Gly Ala Ala Phe Ala
245 250 255

```
Leu Thr Leu Phe Ser Cys Ala Phe Val Gly Thr Arg Leu Leu Phe Pro
            260                 265                 270

Asn Gly Ile Asn Arg Ile Gly Gly Leu Asn Val Ala Met Ile Cys Phe
        275                 280                 285

Ser Val Glu Ile Ile Gly Leu Leu Leu Val Gly Val Ala Thr Met Pro
    290                 295                 300

Trp Met Ala Lys Ile Gly Val Leu Leu Ala Gly Ala Gly Phe Ser Leu
305                 310                 315                 320

Val Phe Pro Ala Leu Gly Val Val Ala Ile Lys Ala Val Pro Gln Gln
                325                 330                 335

Asn Gln Gly Ala Ala Leu Ala Thr Tyr Thr Val Phe Met Asp Leu Ser
            340                 345                 350

Leu Gly Val Thr Gly Pro Leu Ala Gly Leu Val Met Ser Trp Ala Gly
        355                 360                 365

Val Pro Val Ile Tyr Leu Ala Ala Ala Gly Leu Val Ala Ile Ala Leu
    370                 375                 380

Leu Leu Thr Trp Arg Leu Lys Lys Arg Pro Pro Glu His Val Pro Glu
385                 390                 395                 400

Ala Ala Ser Ser Ser
                405


<210> SEQ ID NO 35
<211> LENGTH: 1218
<212> TYPE: DNA
<213> ORGANISM: Artificial Sequence
<220> FEATURE:
<223> OTHER INFORMATION: YhhS(S129G/I241T/D246V/V330I) NT

<400> SEQUENCE: 35

atgcccgaac ccgtagccga acccgcgcta aacggattgc gcctgaattt gcgcattgtc      60

tctatagtca tgtttaactt cgccagctac ctcaccatcg ggttgccgct cgctgtatta     120

ccgggctatg tccatgatgt gatgggcttt agcgccttct gggcaggatt ggttatcagc     180

ctgcaatatt tcgccacctt gctgagccgc cctcatgccg gacgttacgc cgattcgctg     240

ggacccaaaa agattgtcgt cttcggttta tgcggctgct tttgagcggg tctggggtat     300

ctgacggcag gattaaccgc cagtctgcct gtcatcagcc tgttattact ttgcctgggg     360

cgcgtcatcc ttgggattgg gcaaggtttt gccggaacgg gatcgaccct atggggcgtt     420

ggcgtggttg gctcgctgca tatcgggcgg gtgatttcgt ggaacggcat tgtcacttac     480

ggggcgatgg cgatgggtgc gccgttaggc gtcgtgtttt atcactgggg cggcttgcag     540

gcgttagcgt taatcattat gggcgtggcg ctggtggcca ttttgttggc gatcccgcgt     600

ccgacggtaa aagccagtaa aggcaaaccg ctgccgtttc gcgcggtgct tgggcgcgtc     660

tggctgtacg gtatggcgct ggcactggct tccgccggat ttggcgtcat cgccaccttt     720

accacgctgt tttatgtcgc taaaggttgg gacggtgcgg ctttcgcgct gacgctgttt     780

agctgtgcgt ttgtcggtac gcgtttgtta ttccctaacg gcattaaccg tatcggtggc     840

ttaaacgtag cgatgatttg ctttagcgtt gagataatcg gcctgctact ggttggcgtg     900

gcgactatgc cgtggatggc gaaaatcggc gtcttactgg cgggggccgg gttttcgctg     960

gtgttcccgg cattgggtgt agtggcgata aaagcggttc cgcagcaaaa tcagggggcg    1020

gcgctggcaa cttacaccgt atttatggat ttatcgcttg gcgtgactgg accactggct    1080

gggctggtga tgagctgggc gggcgtaccg gtgatttatc tggcggcggc gggactggtc    1140
```

gcaatcgcgt tattactgac gtggcgatta aaaaaacggc ctccggaaca cgtccctgag 1200
gccgcctcat catcttaa 1218

<210> SEQ ID NO 36
<211> LENGTH: 405
<212> TYPE: PRT
<213> ORGANISM: Artificial Sequence
<220> FEATURE:
<223> OTHER INFORMATION: YhhS(S129G/I241Q) AA

<400> SEQUENCE: 36

Met Pro Glu Pro Val Ala Glu Pro Ala Leu Asn Gly Leu Arg Leu Asn
1 5 10 15

Leu Arg Ile Val Ser Ile Val Met Phe Asn Phe Ala Ser Tyr Leu Thr
20 25 30

Ile Gly Leu Pro Leu Ala Val Leu Pro Gly Tyr Val His Asp Val Met
35 40 45

Gly Phe Ser Ala Phe Trp Ala Gly Leu Val Ile Ser Leu Gln Tyr Phe
50 55 60

Ala Thr Leu Leu Ser Arg Pro His Ala Gly Arg Tyr Ala Asp Ser Leu
65 70 75 80

Gly Pro Lys Lys Ile Val Val Phe Gly Leu Cys Gly Cys Phe Leu Ser
85 90 95

Gly Leu Gly Tyr Leu Thr Ala Gly Leu Thr Ala Ser Leu Pro Val Ile
100 105 110

Ser Leu Leu Leu Leu Cys Leu Gly Arg Val Ile Leu Gly Ile Gly Gln
115 120 125

Gly Phe Ala Gly Thr Gly Ser Thr Leu Trp Gly Val Gly Val Val Gly
130 135 140

Ser Leu His Ile Gly Arg Val Ile Ser Trp Asn Gly Ile Val Thr Tyr
145 150 155 160

Gly Ala Met Ala Met Gly Ala Pro Leu Gly Val Val Phe Tyr His Trp
165 170 175

Gly Gly Leu Gln Ala Leu Ala Leu Ile Ile Met Gly Val Ala Leu Val
180 185 190

Ala Ile Leu Leu Ala Ile Pro Arg Pro Thr Val Lys Ala Ser Lys Gly
195 200 205

Lys Pro Leu Pro Phe Arg Ala Val Leu Gly Arg Val Trp Leu Tyr Gly
210 215 220

Met Ala Leu Ala Leu Ala Ser Ala Gly Phe Gly Val Ile Ala Thr Phe
225 230 235 240

Gln Thr Leu Phe Tyr Asp Ala Lys Gly Trp Asp Gly Ala Ala Phe Ala
245 250 255

Leu Thr Leu Phe Ser Cys Ala Phe Val Gly Thr Arg Leu Leu Phe Pro
260 265 270

Asn Gly Ile Asn Arg Ile Gly Gly Leu Asn Val Ala Met Ile Cys Phe
275 280 285

Ser Val Glu Ile Ile Gly Leu Leu Leu Val Gly Val Ala Thr Met Pro
290 295 300

Trp Met Ala Lys Ile Gly Val Leu Leu Ala Gly Ala Gly Phe Ser Leu
305 310 315 320

Val Phe Pro Ala Leu Gly Val Val Ala Val Lys Ala Val Pro Gln Gln
325 330 335

Asn Gln Gly Ala Ala Leu Ala Thr Tyr Thr Val Phe Met Asp Leu Ser
340 345 350

```
Leu Gly Val Thr Gly Pro Leu Ala Gly Leu Val Met Ser Trp Ala Gly
        355                 360                 365

Val Pro Val Ile Tyr Leu Ala Ala Ala Gly Leu Val Ala Ile Ala Leu
    370                 375                 380

Leu Leu Thr Trp Arg Leu Lys Lys Arg Pro Pro Glu His Val Pro Glu
385                 390                 395                 400

Ala Ala Ser Ser Ser
                405


<210> SEQ ID NO 37
<211> LENGTH: 1218
<212> TYPE: DNA
<213> ORGANISM: Artificial Sequence
<220> FEATURE:
<223> OTHER INFORMATION: YhhS(S129G/I241Q) NT

<400> SEQUENCE: 37

atgcccgaac ccgtagccga acccgcgcta aacggattgc gcctgaattt gcgcattgtc      60

tctatagtca tgtttaactt cgccagctac ctcaccatcg ggttgccgct cgctgtatta     120

ccgggctatg tccatgatgt gatgggcttt agcgccttct gggcaggatt ggttatcagc     180

ctgcaatatt tcgccacctt gctgagccgc cctcatgccg gacgttacgc cgattcgctg     240

ggacccaaaa agattgtcgt cttcggttta tgcggctgct tttgagcgg tctggggtat      300

ctgacggcag gattaaccgc cagtctgcct gtcatcagcc tgttattact ttgcctgggg     360

cgcgtcatcc ttgggattgg gcaaggtttt gccggaacgg gatcgaccct atggggcgtt     420

ggcgtggttg gctcgctgca tatcgggcgg gtgatttcgt ggaacggcat tgtcacttac     480

ggggcgatgg cgatgggtgc gccgttaggc gtcgtgtttt atcactgggg cggcttgcag     540

gcgttagcgt taatcattat gggcgtggcg ctggtggcca ttttgttggc gatcccgcgt     600

ccgacggtaa aagccagtaa aggcaaaccg ctgccgtttc gcgcggtgct tgggcgcgtc     660

tggctgtacg gtatggcgct ggcactggct tccgccggat ttggcgtcat cgccaccttt     720

cagacgctgt tttatgacgc taaaggttgg gacggtgcgg ctttcgcgct gacgctgttt     780

agctgtgcgt ttgtcggtac gcgtttgtta ttccctaacg gcattaaccg tatcggtggc     840

ttaaacgtag cgatgatttg ctttagcgtt gagataatcg gcctgctact ggttggcgtg     900

gcgactatgc cgtggatggc gaaaatcggc gtcttactgg cgggggccgg gttttcgctg     960

gtgttcccgg cattgggtgt agtggcggta aaagcggttc cgcagcaaaa tcagggggcg    1020

gcgctggcaa cttacaccgt atttatggat ttatcgcttg gcgtgactgg accactggct    1080

gggctggtga tgagctgggc gggcgtaccg gtgatttatc tggcggcggc gggactggtc    1140

gcaatcgcgt tattactgac gtggcgatta aaaaaacggc ctccggaaca cgtccctgag    1200

gccgcctcat catcttaa                                                  1218


<210> SEQ ID NO 38
<211> LENGTH: 4695
<212> TYPE: DNA
<213> ORGANISM: Artificial Sequence
<220> FEATURE:
<223> OTHER INFORMATION: pSKH130

<400> SEQUENCE: 38

tcgaggccgc gattaaattc caacatggat gctgatttat atgggtataa atgggctcgc      60

gataatgtcg ggcaatcagg tgcgacaatc tatcgattgt atgggaagcc cgatgcgcca     120
```

```
gagttgtttc tgaaacatgg caaaggtagc gttgccaatg atgttacaga tgagatggtc    180
agactaaact ggctgacgga atttatgcct cttccgacca tcaagcattt tatccgtact    240
cctgatgatg catggttact caccactgcg atccccggga aaacagcatt ccaggtatta    300
gaagaatatc ctgattcagg tgaaaatatt gttgatgcgc tggcagtgtt cctgcgccgg    360
ttgcattcga ttcctgtttg taattgtcct tttaacagcg atcgcgtatt tcgtctcgct    420
caggcgcaat cacgaatgaa taacggtttg gttgatgcga gtgattttga tgacgagcgt    480
aatggctggc ctgttgaaca agtctggaaa gaaatgcata agcttttgcc attctcaccg    540
gattcagtcg tcactcatgg tgatttctca cttgataacc ttatttttga cgaggggaaa    600
ttaataggtt gtattgatgt tggacgagtc ggaatcgcag accgatacca ggatcttgcc    660
atcctatgga actgcctcgg tgagttttct ccttcattac agaaacggct ttttcaaaaa    720
tatggtattg ataatcctga tatgaataaa ttgcagtttc atttgatgct cgatgagttt    780
ttctaatcag aattggttaa ttggttgtaa cactggcaga gcattacgct gacttgacgg    840
gacggcggct ttgttgaata aatcgaactt ttgctgagtt gaaggatcag atcacgcatc    900
ttcccgacaa cgcagaccgt tccgtggcaa agcaaaagtt caaaatcacc aactggtcca    960
cctacaacaa agctctcatc aaccgtggct ccctcacttt ctggctggat gatggggcga   1020
ttcaggcctg gtatgagtca gcaacacctt cttcacgagg cagacctcag cgctcaaaga   1080
tgcaggggta aaagctaacc gcatctttac cgacaaggca tccggcagtt caacagatcg   1140
ggaagggctg gatttgctga ggatgaaggt ggaggaaggt gatgtcattc tggtgaagaa   1200
gctcgaccgt cttggccgcg acaccgccga catgatccaa ctgataaaag agtttgatgc   1260
tcagggtgta gcggttcggt ttattgacga cgggatcagt accgacggtg atatggggca   1320
aatggtggtc accgcgcgta atacgactca ctatagggcg aattggagct ccaccgcggt   1380
ggcggccgct ctagacttta cggtatcgcc gctcccgatt cgcagcgcat cgccttctat   1440
cgccttcttg acgagttctt ctgagcggga ctctggggtt cgctagagga tcgatccttt   1500
ttaacccatc acatatacct gccgttcact attatttagt gaaatgagat attatgatat   1560
tttctgaatt gtgattaaaa aggcaacttt atgcccatgc aacagaaact ataaaaaata   1620
cagagaatga aaagaaacag atagattttt tagttcttta ggcccgtagt ctgcaaatcc   1680
ttttatgatt ttctatcaaa caaaagagga aaatagacca gttgcaatcc aaacgagagt   1740
ctaatagaat gaggtcgaaa agtaaatcgc gcgggtttgt tactgataaa gcaggcaaga   1800
cctaaaatgt gtaaagggca aagtgtatac tttggcgtca ccccttacat attttaggtc   1860
tttttttatt gtgcgtaact aacttgccat cttcaaacag gagggctgga agaagcagac   1920
cgctaacaca gtacataaaa aaggagacat gaacgatgaa catcaaaaag tttgcaaaac   1980
aagcaacagt attaaccttt actaccgcac tgctggcagg aggcgcaact caagcgtttg   2040
cgaaagaaac gaaccaaaag ccatataagg aaacatacgg catttcccat attacacgcc   2100
atgatatgct gcaaatccct gaacagcaaa aaaatgaaaa atatcaagtt cctgaattcg   2160
attcgtccac aattaaaaat atctcttctg caaaaggcct ggacgtttgg gacagctggc   2220
cattacaaaa cgctgacggc actgtcgcaa actatcacgg ctaccacatc gtctttgcat   2280
tagccggaga tcctaaaaat gcggatgaca catcgattta catgttctat caaaaagtcg   2340
gcgaaacttc tattgacagc tggaaaaacg ctggccgcgt ctttaaagac agcgacaaat   2400
tcgatgcaaa tgattctatc ctaaaagacc aaacacaaga atggtcaggt tcagccacat   2460
ttacatctga cggaaaaatc cgtttattct acactgattt ctccggtaaa cattacggca   2520
```

-continued aacaaacact gacaactgca caagttaacg tatcagcatc agacagctct ttgaacatca 2580
acggtgtaga ggattataaa tcaatctttg acggtgacgg aaaaacgtat caaaatgtac 2640
agcagttcat cgatgaaggc aactacagct caggcgacaa ccatacgctg agagatcctc 2700
actacgtaga agataaaggc cacaaatact tagtatttga agcaaacact ggaactgaag 2760
atggctacca aggcgaagaa tctttattta acaaagcata ctatggcaaa agcacatcat 2820
tcttccgtca agaaagtcaa aaacttctgc aaagcgataa aaaacgcacg gctgagttag 2880
caaacggcgc tctcggtatg attgagctaa acgatgatta cacactgaaa aaagtgatga 2940
aaccgctgat tgcatctaac acagtaacag atgaaattga acgcgcgaac gtctttaaaa 3000
tgaacggcaa atggtacctg ttcactgact cccgcggatc aaaaatgacg attgacggca 3060
ttacgtctaa cgatatttac atgcttggtt atgtttctaa ttctttaact ggcccataca 3120
agccgctgaa caaaactggc cttgtgttaa aaatggatct tgatcctaac gatgtaacct 3180
ttacttactc acacttcgct gtacctcaag cgaaaggaaa caatgtcgtg attacaagct 3240
atatgacaaa cagaggattc tacgcagaca aacaatcaac gtttgcgcca agcttcctgc 3300
tgaacatcaa aggcaagaaa acatctgttg tcaaagacag catccttgaa caaggacaat 3360
taacagttaa caaataaaaa cgcaaaagaa aatgccgatg ggtaccgagc gaaatgaccg 3420
accaagcgac gcccaacctg ccatcggatc ccccgggctg caggaattcg atatcacgct 3480
agtcgaccta gctagcatat ggggagatct actagtaaag catgccaatt ggtattctat 3540
agtgtcacct aaatcgtatg tgtatgatac ataaggttat gtattaattg tagccgcgtt 3600
ctaacgacaa tatgtacaag cctaattgtg tagcatctgg cttactgaag cagaccctat 3660
catctctctc gtaaactgcc gtcagagtcg gtttggttgg acgaaccttc tgagtttctg 3720
gtaacgccgt cccgcacccg gaaatggtca gcgaaccaat cagcagggtc atcgctagcc 3780
catggctaat tcccatgtca gccgttaagt gttcctgtgt cactcaaaat tgctttgaga 3840
ggctctaagg gcttctcagt gcgttacatc cctggcttgt tgtccacaac cgttaaacct 3900
taaaagcttt aaaagcctta tatattcttt tttttcttat aaaacttaaa accttagagg 3960
ctatttaagt tgctgattta tattaatttt attgttcaaa catgagagct tagtacgtga 4020
aacatgagag cttagtacgt tagccatgag agcttagtac gttagccatg agggtttagt 4080
tcgttaaaca tgagagctta gtacgttaaa catgagagct tagtacgtga aacatgagag 4140
cttagtacgt actatcaaca ggttgaactg ctgatcttca gatcctctac gccggacgca 4200
tcgtggccgg atcttgcggc cgcaaaaatt aaaaatgaag ttttaaatca atctaaagta 4260
tatatgagta aacttggtct gacagttacc aatgcttaat cagtgaggca ccaataactg 4320
ccttaaaaaa actagcgctg aggtctgcct cgtgaagaag gtgttgctga ctcataccag 4380
gcctgaatcg ccccatcatc cagccagaaa gtgagggagc cacggttgat gagagctttg 4440
ttgtaggtgg accagttggt gattttgaac ttttgctttg ccacggaacg gtctgcgttg 4500
tcgggaagat gcgtgatctg atccttcaac tcagcaaaag ttcgatttat tcaacaaagc 4560
cacgttgtgt ctcaaaatct ctgatgttac attgcacaag ataaaaatat atcatcatga 4620
acaataaaac tgtctgctta cataaacagt aatacaaggg gtgttatgag ccatattcaa 4680
cgggaaacgt cttgc 4695